(12) United States Patent
Hyde et al.

(10) Patent No.: US 8,642,093 B2
(45) Date of Patent: Feb. 4, 2014

(54) METHODS AND SYSTEMS FOR USE OF PHOTOLYZABLE NITRIC OXIDE DONORS

(75) Inventors: Roderick A. Hyde, Redmond, WA (US); Muriel Y. Ishikawa, Livermore, CA (US); Lowell L. Wood, Jr., Bellevue, WA (US)

(73) Assignee: The Invention Science Fund I, LLC, Bellevue, WA (US)

( * ) Notice: Subject to any disclaimer, the term of this patent is extended or adjusted under 35 U.S.C. 154(b) by 1529 days.

(21) Appl. No.: 11/981,743

(22) Filed: Oct. 30, 2007

(65) Prior Publication Data

US 2009/0110712 A1    Apr. 30, 2009

(51) Int. Cl.
A61K 31/04    (2006.01)
A61N 5/06    (2006.01)

(52) U.S. Cl.
USPC ............................................. 424/718; 607/88

(58) Field of Classification Search
USPC ..................... 424/423, 718; 607/88
See application file for complete search history.

(56) References Cited

U.S. PATENT DOCUMENTS

| | | |
|---|---|---|
| 3,918,967 A | 11/1975 | Krohn et al. |
| 4,162,536 A | 7/1979 | Morley |
| 4,210,697 A | 7/1980 | Adiletta |
| 4,248,214 A | 2/1981 | Hannah et al. |
| 4,561,429 A | 12/1985 | Sato et al. |
| 4,611,594 A | 9/1986 | Grayhack et al. |
| 4,919,149 A | 4/1990 | Stang |
| 5,109,871 A | 5/1992 | Thornton |
| 5,279,294 A | 1/1994 | Anderson et al. |
| 5,351,698 A | 10/1994 | Wheeler et al. |
| 5,366,997 A | 11/1994 | Keefer et al. |
| 5,374,710 A | 12/1994 | Tsien et al. |
| 5,405,919 A | 4/1995 | Keefer et al. |
| 5,495,961 A | 3/1996 | Maestre |
| 5,530,263 A | 6/1996 | DiVincenzo |
| 5,567,302 A | 10/1996 | Song et al. |
| 5,571,152 A | 11/1996 | Chen et al. |
| 5,580,433 A | 12/1996 | Baker et al. |
| 5,665,077 A | 9/1997 | Rosen et al. |
| 5,676,963 A | 10/1997 | Keefer et al. |
| 5,683,668 A | 11/1997 | Hrabie et al. |
| 5,690,777 A | 11/1997 | Kuethe et al. |
| 5,692,520 A | 12/1997 | Lavoisier |
| 5,736,152 A | 4/1998 | Dunn |
| 5,741,815 A | 4/1998 | Lai |
| 5,765,558 A | 6/1998 | Psaros et al. |
| 5,814,666 A | 9/1998 | Green et al. |
| 5,858,799 A | 1/1999 | Yee et al. |
| 5,900,433 A | 5/1999 | Igo et al. |
| 5,910,316 A | 6/1999 | Keefer et al. |
| 5,943,160 A | 8/1999 | Downing |
| 5,956,172 A | 9/1999 | Downing |
| 5,980,705 A | 11/1999 | Allen et al. |
| 5,994,444 A | 11/1999 | Trescony et al. |
| 6,000,398 A | 12/1999 | Alla et al. |
| 6,037,346 A | 3/2000 | Doherty, Jr. et al. |
| 6,080,110 A | 6/2000 | Thorgersen |
| 6,100,096 A | 8/2000 | Bollinger et al. |
| 6,103,765 A | 8/2000 | Neal |
| 6,127,363 A | 10/2000 | Doherty, Jr. et al. |
| 6,143,314 A | 11/2000 | Chandrashekar et al. |
| 6,149,606 A | 11/2000 | Alving et al. |
| 6,156,753 A | 12/2000 | Doherty, Jr. et al. |
| 6,182,661 B1 | 2/2001 | Solanki et al. |
| 6,190,704 B1 | 2/2001 | Murrell |
| 6,223,747 B1 | 5/2001 | Rudge et al. |
| 6,241,752 B1 | 6/2001 | Sheinman et al. |
| 6,265,420 B1 | 7/2001 | Lai |
| 6,280,604 B1 | 8/2001 | Allen et al. |
| 6,287,601 B1 | 9/2001 | Russell |
| 6,306,609 B1 | 10/2001 | Lai |
| 6,308,708 B2 | 10/2001 | Strauss et al. |
| 6,321,751 B1 | 11/2001 | Strauss et al. |
| 6,327,074 B1 | 12/2001 | Bass et al. |
| 6,341,607 B1 | 1/2002 | Couvreur |
| 6,369,071 B1 | 4/2002 | Haj-Yehia |
| 6,432,077 B1 | 8/2002 | Stenzler |
| 6,436,470 B1 | 8/2002 | Iacocca et al. |
| 6,440,498 B2 | 8/2002 | Schaller |
| 6,443,978 B1 | 9/2002 | Zharov |
| 6,451,337 B1 | 9/2002 | Smith et al. |
| 6,469,051 B2 | 10/2002 | Nagano et al. |
| 6,559,184 B2 | 5/2003 | Neal |
| 6,621,687 B2 | 9/2003 | Lewis, Jr. et al. |
| 6,635,273 B1 | 10/2003 | Loscalzo et al. |
| 6,635,415 B1 | 10/2003 | Bollinger et al. |
| 6,636,652 B1 | 10/2003 | Kopelman et al. |
| 6,639,007 B2 | 10/2003 | Plamthottam |
| 6,651,667 B2 | 11/2003 | Osterberg |
| 6,673,338 B1 | 1/2004 | Arnold et al. |
| 6,673,871 B2 | 1/2004 | Warneke et al. |
| 6,682,863 B2 | 1/2004 | Rivers et al. |
| 6,696,072 B1 | 2/2004 | Podolski |
| 6,706,274 B2 | 3/2004 | Herrmann et al. |
| 6,743,249 B1 | 6/2004 | Alden |
| 6,747,062 B2 | 6/2004 | Murrell |
| 6,773,714 B2 | 8/2004 | Dunn et al. |
| 6,812,500 B2 | 11/2004 | Reeh et al. |
| 6,818,356 B1 | 11/2004 | Bates |
| 6,840,244 B2 | 1/2005 | Kemp |
| 6,841,166 B1 | 1/2005 | Zhang et al. |
| 6,900,891 B2 | 5/2005 | Kopelman et al. |

(Continued)

FOREIGN PATENT DOCUMENTS

DE    20115123 U1    6/2001
EP    1 704 877 A1    9/2006

(Continued)

OTHER PUBLICATIONS

Butler, P. et al.; "Cell Transplantation from Limb Allografts"; Plastic and Reconstructive Surgery; Bearing a date of Jul. 1998; pp. 161-168 (11 total pages); vol. 102, No. 1; American Society of Plastic Surgeons; located at: http://www.plasreconsurg.com; printed on Apr. 25, 2008.

(Continued)

Primary Examiner — Samantha Shterengarts

(57) ABSTRACT

The present disclosure relates to methods and systems for use of photolyzable nitric oxide donors for the treatment of sexual dysfunction.

26 Claims, 8 Drawing Sheets

(56) References Cited

U.S. PATENT DOCUMENTS

| | | |
|---|---|---|
| 6,943,166 B1 | 9/2005 | Pullman et al. |
| 6,969,507 B2 * | 11/2005 | Weisskoff et al. ............ 424/9.2 |
| 6,983,751 B2 | 1/2006 | Osterberg |
| 6,994,934 B2 | 2/2006 | Stanish et al. |
| 7,052,711 B2 | 5/2006 | West et al. |
| 7,088,040 B1 | 8/2006 | Ducharme et al. |
| 7,105,502 B2 | 9/2006 | Arnold et al. |
| 7,105,607 B2 | 9/2006 | Chen |
| 7,122,046 B2 | 10/2006 | Augustine et al. |
| 7,122,529 B2 | 10/2006 | Ruane et al. |
| 7,144,655 B2 | 12/2006 | Jenson et al. |
| 7,181,174 B2 | 2/2007 | Fitzgibbon et al. |
| 7,181,261 B2 | 2/2007 | Silver et al. |
| 7,183,001 B1 | 2/2007 | Ederle et al. |
| 7,189,471 B2 | 3/2007 | Jankowksi et al. |
| 7,194,801 B2 | 3/2007 | Jenson et al. |
| 7,206,605 B2 | 4/2007 | Hattori |
| 7,210,817 B2 | 5/2007 | Lee et al. |
| 7,215,687 B2 | 5/2007 | Kawai et al. |
| 7,215,887 B2 | 5/2007 | Ternullo et al. |
| 7,217,882 B2 | 5/2007 | Walukiewicz et al. |
| 7,218,900 B2 | 5/2007 | Suzuki |
| 7,220,258 B2 | 5/2007 | Myhr |
| 7,227,956 B1 | 6/2007 | Onishi |
| 7,235,189 B2 | 6/2007 | Höhn et al. |
| 7,235,361 B2 | 6/2007 | Bawendi et al. |
| 7,235,505 B2 | 6/2007 | Gromelski et al. |
| 7,236,595 B1 | 6/2007 | Bean et al. |
| 7,238,628 B2 | 7/2007 | Demaray et al. |
| 7,245,894 B2 | 7/2007 | Sekiguchi et al. |
| RE39,785 E | 8/2007 | Fuse |
| 7,253,953 B2 | 8/2007 | Browning |
| 7,254,160 B2 | 8/2007 | Kawamoto et al. |
| 7,256,923 B2 | 8/2007 | Liu et al. |
| 7,257,327 B2 | 8/2007 | Small |
| 7,260,155 B2 | 8/2007 | Stonick et al. |
| 7,260,402 B1 | 8/2007 | Ahmed |
| 7,260,764 B2 | 8/2007 | Chen |
| 7,260,768 B1 | 8/2007 | Matsumoto et al. |
| 7,261,693 B2 | 8/2007 | Wilcox et al. |
| 7,264,602 B1 | 9/2007 | Longsworth |
| 7,273,567 B1 | 9/2007 | Wellinghoff et al. |
| 7,280,811 B2 | 10/2007 | Sugiyama et al. |
| 7,283,710 B2 | 10/2007 | Sano et al. |
| 7,294,678 B2 | 11/2007 | McGlothlin et al. |
| 7,294,779 B2 | 11/2007 | Watabe et al. |
| 7,295,737 B2 | 11/2007 | Moorjani et al. |
| 7,295,741 B2 | 11/2007 | Sako et al. |
| 7,298,605 B2 | 11/2007 | Itoh et al. |
| 7,298,977 B2 | 11/2007 | Ohsawa et al. |
| 7,301,751 B2 | 11/2007 | Lee et al. |
| 7,301,754 B1 | 11/2007 | Knowles |
| 7,303,333 B2 | 12/2007 | Yu |
| 7,418,399 B2 | 8/2008 | Schaeffer et al. |
| 7,449,595 B2 * | 11/2008 | Garvey et al. ................ 560/121 |
| 7,582,623 B2 | 9/2009 | Mascharak |
| 7,603,166 B2 | 10/2009 | Casscells, III et al. |
| 7,829,553 B2 | 11/2010 | Arnold et al. |
| 7,899,539 B2 | 3/2011 | Whitehurst et al. |
| 2001/0007080 A1 | 7/2001 | Sheinman et al. |
| 2002/0022046 A1 | 2/2002 | Tedeschi et al. |
| 2002/0026937 A1 | 3/2002 | Mault |
| 2002/0055702 A1 | 5/2002 | Atala et al. |
| 2002/0068365 A1 | 6/2002 | Kuhrts |
| 2002/0138051 A1 | 9/2002 | Hole et al. |
| 2002/0165179 A1 | 11/2002 | Baker, Jr. |
| 2002/0188323 A1 | 12/2002 | Penner et al. |
| 2003/0009127 A1 | 1/2003 | Trescony et al. |
| 2003/0039697 A1 | 2/2003 | Zhao et al. |
| 2003/0073133 A1 | 4/2003 | Leyland-Jones |
| 2003/0077243 A1 | 4/2003 | Fitzhugh et al. |
| 2003/0088191 A1 | 5/2003 | Freeman et al. |
| 2003/0093143 A1 | 5/2003 | Zhao et al. |
| 2003/0165578 A1 | 9/2003 | Murrell |
| 2003/0203915 A1 * | 10/2003 | Fang et al. ............... 514/253.01 |
| 2004/0009238 A1 | 1/2004 | Miller et al. |
| 2004/0013747 A1 | 1/2004 | Tucker et al. |
| 2004/0072360 A1 | 4/2004 | Naaman et al. |
| 2004/0081580 A1 | 4/2004 | Hole et al. |
| 2004/0087831 A1 | 5/2004 | Michels et al. |
| 2004/0193218 A1 | 9/2004 | Butler |
| 2004/0209869 A1 | 10/2004 | Landau et al. |
| 2004/0247640 A1 | 12/2004 | Zhao et al. |
| 2005/0053106 A1 | 3/2005 | Herron et al. |
| 2005/0079148 A1 | 4/2005 | Fitzhugh et al. |
| 2005/0136483 A1 | 6/2005 | Carlson |
| 2005/0181026 A1 | 8/2005 | Davis et al. |
| 2005/0197682 A1 * | 9/2005 | Fox et al. ....................... 607/88 |
| 2005/0203069 A1 | 9/2005 | Arnold et al. |
| 2005/0220838 A1 | 10/2005 | Zhao et al. |
| 2005/0238704 A1 | 10/2005 | Zumbrunn et al. |
| 2005/0249667 A1 | 11/2005 | Tuszynski et al. |
| 2005/0267090 A1 | 12/2005 | Mascharak |
| 2005/0286916 A1 | 12/2005 | Nakazato et al. |
| 2006/0074282 A1 | 4/2006 | Ward et al. |
| 2006/0134728 A1 | 6/2006 | MacDonald et al. |
| 2006/0206171 A1 | 9/2006 | Gertner et al. |
| 2006/0206173 A1 | 9/2006 | Gertner et al. |
| 2006/0235493 A1 | 10/2006 | Dotson |
| 2006/0275350 A1 | 12/2006 | Davis et al. |
| 2006/0280307 A1 | 12/2006 | Ikushima et al. |
| 2007/0021382 A1 | 1/2007 | Assaf et al. |
| 2007/0053996 A1 | 3/2007 | Boyden et al. |
| 2007/0054319 A1 | 3/2007 | Boyden et al. |
| 2007/0059351 A1 | 3/2007 | Murrell et al. |
| 2007/0065473 A1 | 3/2007 | Miller |
| 2007/0088316 A1 | 4/2007 | Stenzler et al. |
| 2007/0148117 A1 | 6/2007 | Davis et al. |
| 2007/0166357 A1 | 7/2007 | Shaffer et al. |
| 2007/0181444 A1 | 8/2007 | Bernstein et al. |
| 2007/0190122 A1 | 8/2007 | Davis et al. |
| 2007/0208395 A1 | 9/2007 | Leclerc et al. |
| 2007/0233208 A1 | 10/2007 | Kurtz et al. |
| 2007/0274874 A1 | 11/2007 | Miller et al. |
| 2007/0298354 A1 * | 12/2007 | Ding et al. ..................... 430/320 |
| 2008/0069863 A1 | 3/2008 | Peters |
| 2008/0097282 A1 | 4/2008 | Hole et al. |
| 2008/0220048 A1 | 9/2008 | Chen et al. |
| 2008/0281383 A1 | 11/2008 | Butler |
| 2008/0286321 A1 | 11/2008 | Reneker et al. |
| 2008/0311163 A1 | 12/2008 | Peters |
| 2009/0024063 A1 | 1/2009 | Kalvatanond |
| 2009/0081279 A1 | 3/2009 | Jezek et al. |
| 2009/0118710 A1 | 5/2009 | Kortzeborn |
| 2009/0202617 A1 | 8/2009 | Ward et al. |
| 2009/0204057 A1 | 8/2009 | Woo et al. |
| 2009/0214618 A1 | 8/2009 | Schoenfisch et al. |
| 2009/0214624 A1 | 8/2009 | Smith et al. |
| 2010/0081144 A1 | 4/2010 | Holmes et al. |
| 2010/0098733 A1 | 4/2010 | Stasko |
| 2010/0152683 A1 | 6/2010 | Lindgren et al. |
| 2010/0197802 A1 | 8/2010 | Jezek et al. |
| 2011/0008815 A1 | 1/2011 | Stamler et al. |
| 2011/0033437 A1 | 2/2011 | Smith et al. |

FOREIGN PATENT DOCUMENTS

| | | |
|---|---|---|
| WO | WO 92/09962 | 6/1992 |
| WO | WO 96/08966 A1 | 3/1996 |
| WO | WO 00/53193 | 9/2000 |
| WO | WO 01/10344 A1 | 2/2001 |
| WO | WO 02/17898 A2 | 3/2002 |
| WO | WO 02/057738 A2 | 7/2002 |
| WO | WO 03/006427 A1 | 1/2003 |
| WO | WO 03/086282 A2 | 10/2003 |
| WO | WO 2005/070008 A2 | 8/2005 |
| WO | WO 2005/112954 A1 | 12/2005 |
| WO | WO 2006/084912 A1 | 8/2006 |
| WO | WO 2006/095193 A2 | 9/2006 |
| WO | WO 2006/100155 A1 | 9/2006 |
| WO | WO 2006/107122 A1 | 10/2006 |
| WO | WO 2006/108420 A1 | 10/2006 |

(56) References Cited

FOREIGN PATENT DOCUMENTS

| WO | WO 2007/130702 A2 | 11/2007 |
|---|---|---|
| WO | WO 2008/046211 A1 | 4/2008 |
| WO | WO 2009/131931 A1 | 10/2009 |

OTHER PUBLICATIONS

Butler, A.R.; Nicholson, R.; *Life, Death and Nitric Oxide*; Bearing a date of Oct. 17, 2003; 1st edition; Royal Society of Chemistry; ISBN 978-0854046867 (Not Provided).
U.S. Appl. No. 12/148,284, Hyde et al.
U.S. Appl. No. 12/148,283, Hyde et al.
De Lima, R.G. et al.; "Controlled Nitric Oxide Photo-Release From Nitro Ruthenium Complexes: The Vasodilator Response Produced by UV Light Irradiation"; Inorganica Chimica Acta; Bearing a date of 2005; pp. 2643-2650; vol. 358; Elsevier B.V.; located at: http://www.sciencedirect.com.
Frank, S. et al.; "Nitric Oxide Triggers Enhanced Induction of Vascular Endothelial Growth Factor Expression in Cultured Keratinocytes (HaCaT) and During Cutaneous Wound Repair"; The FASEB Journal; Bearing a date of 1999; pp. 2002-2014; vol. 13.
Ghaffari, A. et al.; "A Direct Nitric Oxide Gas Delivery System for Bacterial and Mammalian Cell Cultures"; Nitric Oxide; Bearing a date of 2005; pp. 129-140; vol. 12; Elsevier Inc.; located at: http://www.sciencedirect.com.
Ghaffari, A. et al.; "Efficacy of Gaseous Nitric Oxide in the Treatment of Skin and Soft Tissue Infections"; Wound Repair and Regeneration; Bearing a date of 2007; pp. 368-377; vol. 15; Wound Healing Society.
Ghaffari, A. et al.; "Potential Application of Gaseous Nitric Oxide as a Topical Antimicrobial Agent"; Nitric Oxide; Bearing a date of 2006; pp. 21-29; vol. 14; Elsevier Inc.; located at: http://www.sciencedirect.com.
Goldsmith, P.C. et al.; "Inhibitors of Nitric Oxide Synthase in Human Skin"; The Journal of Investigative Dermatology; Bearing a date of Jan. 1996; pp. 113-118; vol. 106, No. 1; The Society for Investigative Dermatology, Inc.
Govers, R.; Rabelink, T.J.; "Cellular Regulation of Endothelial Nitric Oxide Synthase"; Am. J. Physiol. Renal. Physiol.; Bearing a date of 2001; pp. F193-F206; vol. 280; The American Physiological Society; located at: http://www.ajprenal.org.
Guo, H.; "Two-and Three-Photon Upconversion of LaOBr:$Er^{3+}$"; Optical Materials; Bearing a date of 2007; pp. 1840-1843; vol. 29; Elsevier B.V.; located at: http://www.sciencedirect.com.
Hassett, D.J.; Imlay, J.A.; "Bactericidal Antibiotics and Oxidative Stress: A Radical Proposal"; ACS Chemical Biology; Bearing a date of 2007; pp. 708-710; vol. 2, No. 11; located at: http://www.acschemicalbiology.org.
Miller, C.C. et al.; "Treatment of Chronic Nonhealing Leg Ulceration with Gaseous Nitric Oxide: A Case Study"; Journal of Cutaneous Medicine and Surgery; Bearing a date of Aug. 2004; pp. 233-238; vol. 8, No. 4.
Pacher, P. et al.; "Nitric Oxide and Peroxynitrite in Health and Disease"; Physiol. Rev.; Bearing a date of Jan. 2007; pp. 315-424; vol. 87; The American Physiological Society; located at: http://www.prv.org.
Patel, D.N. et al.; "Spectroscopic and Two-Photon Upconversion Studies of $Ho^{3+}$-Doped $Lu_3Al_5O_{12}$"; Optical Materials; Bearing a date of Jul. 1998; pp. 225-234; vol. 10; Elsevier Science B.V.
Rapaport, A. et al.; "Review of the Properties of Up-Conversion Phosphors for New Emissive Displays"; Journal of Display Technology; Bearing a date of Mar. 2006; pp. 68-78; vol. 2, No. 1; IEEE.
Roméro-Graillet, C. et al.; "Nitric Oxide Produced by Ultraviolet-Irradiated Keratinocytes Stimulates Melanogenesis"; J. Clin. Invest.; Bearing a date of Feb. 1997; pp. 635-642; vol. 99, No. 4; The American Society of Clinical Investigation, Inc.
Seabra, A.B. et al.; "S-Nitrosoglutathione Incorporated in Poly(Ethylene Glycol) Matrix: Potential Use for Topical Nitric Oxide Delivery"; Nitric Oxide; Bearing a date of 2004; pp. 263-272; vol. 11; Elsevier Inc.; located at: http://www.sciencedirect.com.

Shabani, M. et al.; "Enhancement of Wound Repair with a Topically Applied Nitric Oxide-Releasing Polymer"; Wound Repair and Regeneration; Bearing dates of Jul.-Sep. 1996; pp. 353-362; vol. 4, No. 3; The Wound Healing Society.
Sussman, C.; *Wound Care: A Collaborative Practice Manual*; Bearing a date of Jan. 2007; ISBN 0781774446 (Not Provided).
Suzuki, H.; Hewitt, C.W.; "Cell Transplantation from Limb Allografts: Discussion"; Plastic and Reconstructive Surgery; Bearing a date of Jul. 1998; pp. 169-170 (2 total pages); vol. 102, No. 1; American Society of Plastic Surgeons; located at: http://www.plasreconsurg.com; printed on May 2, 2008.
Tamir, S.; Tannenbaum, S.R.; "The Role of Nitric Oxide (NO) in the Carcinogenic Process"; Biochimica et Biophysica Acta; Bearing a date of 1996; pp. F31-F36; vol. 1288; Elsevier Science B.V.
Tu, H. et al.; "A Novel Electrochemical Microsensor for Nitric Oxide Based on Electropolymerized Film of o-Aminobenzaldehyde-Ethylene-Diamine Nickel"; Electroanalysis; Bearing a date of 1999; pp. 70-74; vol. 11, No. 1; Wiley-VCH.
Van Faassen, E., Vanin, A. (Eds); *Radicals for Life: The Various Forms of Nitric Oxide*; Bearing a date of Mar. 2007; 442 pages; ISBN 978-0-444-52236-8; Elsevier (Not Provided).
Weller, R. et al.; "Antimicrobial Effect of Acidified Nitrite on Dermatophyte Fungi, *Candida* and Bacterial Skin Pathogens"; Journal of Applied Microbiology; Bearing a date of 2001; pp. 648-652; vol. 90; The Society for Applied Microbiology.
Weller, R. et al.; "Nitric Oxide Is Generated on the Skin Surface by Reduction of Sweat Nitrate"; The Journal of Investigative Dermatology; Bearing a date of Sep. 1996; pp. 327-331; vol. 107, No. 3; The Society of Investigative Dermatology, Inc.
Yamasaki, K. et al.; "Reversal of Impaired Wound Repair in iNOS-Deficient Mice by Topical Adenoviral-Mediated iNOS Gene Transfer"; J. Clin. Invest.; Bearing a date of Mar. 1998; pp. 967-971; vol. 101, No. 5; The American Society for Clinical Investigation, Inc.; located at: http://www.jci.org.
Zhelyaskov, V.R.; Godwin, D.W.; "Photolytic Generation of Nitric Oxide Through a Porous Glass Partitioning Membrane"; Nitric Oxide: Biology and Chemistry; Bearing a date of 1998; pp. 454-459; vol. 2, No. 6; Article No. NO980195; Academic Press.
Stubbington, Tommy; "New Condom Nears Approval"; The Wall Street Journal Online; bearing at date of Apr. 20, 2011; pp. 1-2; 13:18; Dow Jones & Company, Inc.
"A Method of Nitric Oxide Delivery for Healing and Organ Preservation"; University of Texas at Dallas; bearing a date of May 18, 2009; p. 1; located at http://utdallas,technologypublisher.com/TechnologyProject.aspx?id=2302.
"Nanotechnology bandage speeds up healing"; Nanowerk News; Source: Akron Beacon Journal (Paula Schleis); bearing a date of Dec. 15, 2006; pp. 1-2; printed on Jul. 14, 2009; located at http://www.nanowerk.com/news/newsid=1156.php.
Andrews, Karen L. et al.; "A Photosensitive Vascular Smooth Muscle Store of Nitric Oxide in Mouse Aorta: No Dependence on Expression of Endothelial Nitric Oxide Synthase"; British Journal of Pharmacology; 2003; pp. 932-940; vol. 138; Nature Publishing Group.
Bonaventura, Daniella et al.; "A Macrocyclic Nitrosyl Ruthenium Complex is a NO Donor that Induces Rat Aorta Relaxation"; Nitric Oxide; Mar. 2004; pp. 83-91 (p. 1); vol. 10, Issue 2; located at: http://www.sciencedirect.com; printed on Oct. 26, 2007 (Abstract Only).
Chmura, Antonina et al.; "The Role of Photoinduced Electron Transfer Processes in Photodegradation of the $[Fe_4(\mu_3\text{-}S)_3(NO)_7]$ Cluster"; Nitric Oxide; Dec. 2006; pp. 370-379 (p. 1); vol. 15, Issue 4; located at: http://www.sciencedirect.com; printed on Oct. 26, 2007 (Abstract Only).
Chen, X; Gillis, CN; "Methylene Blue Enhanced Photorelaxation in Aorta, Pulmonary Artery and Corpus Cavernosum"; Biochem. Biophys. Res. Commun.; Jan. 29, 1993; pp. 559-563 (pp. 1-2); vol. 190, No. 2; located at: http://www.pubmed.gov; printed on Oct. 26, 2007 (Abstract Only).
Dujić, Željko et al; "Aerobic Exercise Before Diving Reduces Venous Gas Bubble Formation in Humans"; J. Physiol.; 2004; pp. 637-642; vol. 555.3; The Physiological Society.

(56) References Cited

OTHER PUBLICATIONS

"Easy Life II"; Photon Technology International; pp. 1-3; located at: http://www.pti-nj.com/EasyLife/easylife.html; printed on Oct. 6, 2007.
Ferezin, Camila Z. et al; "The Complex Trans-[RuC1([15]aneN$_4$)NO]$^{2+}$ Induces Rat Aorta Relaxation by Ultraviolet Light Irradiation"; Nitric Oxide; Nov. 2005; pp. 170-175 (p. 1); vol. 13, Issue 3; located at: http://www.sciencedirect.com; printed on Oct. 26, 2007 (Abstract Only).
Flitney, FW et al.; "Iron-Sulphur Cluster Nitrosyls, a Novel Class of Nitric Oxide Generator: Mechanism of Vasodilator Action on Rat Isolated Tail Artery"; Br. J. Pharmacol.; Nov. 1992; pp. 842-848 (pp. 1-2); vol. 107, No. 3; located at: http://www.pubmed.gov; printed on Oct. 26, 2007 (Abstract Only).
Flitney, Frederick Werner; Megson, Ian L.; "Nitric Oxide and the Mechanism of Rat Vascular Smooth Muscle Photorelaxation"; J. Physiol.; 2003; pp. 819-828; vol. 550.3; The Physiological Society.
Flitney, FW et al.; "Vasodilator Responses of Rat Isolated Tail Artery Enhanced by Oxygen-Dependent, Photochemical Release of Nitric Oxide from Iron-Sulphur-Nitrosyls"; Br. J. Pharmacol.; Apr. 1996; pp. 1549-1557 (pp. 1-2); vol. 117, No. 7; located at: http://www.pubmed.gov; printed on Oct. 26, 2007 (Abstract Only).
Fukuhara, Kiyoshi et al.; "Photochemical Generation of Nitric Oxide from 6-Nitrobenzo[α]pyrene"; J. Am. Chem. Soc.; 2001; pp. 8662-8666 (p. 1); vol. 123, No. 36; located at: http://pubs.acs.org/cgi-bin/abstract.cgi/jacsat/2001/123/i36/abs/ja0109038.html; printed on Oct. 26, 2007 (Abstract Only).
Gaston, Benjamin; "Summary: Systemic Effects of Inhaled Nitric Oxide"; Proceedings of the American Thoracic Society; 2006; pp. 170-172; vol. 3.
Hardwick, J.B.J. et al.; "A Novel Method for the Delivery of Nitric Oxide Therapy to the Skin of Human Subjects Using a Semi-Permeable Membrane"; Clinical Science; 2001; pp. 395-400; vol. 100; The Biochemical Society and the Medical Research Society.
"OL 770-LED: High-Speed LED Measurement System"; Bearing a date of 2001; pp. 1-6; located at: http://www.optroniclabs.com; Optronic Laboratories, Inc.
"InNo-T Nitric Oxide Measurement System"; Warner Instruments; Bearing dates of 1998-2007; pp. 1-2; located at: http://www.warneronline.com/product_info.cfm?ID=220; printed on Oct. 24, 2007.
Keefer, Larry K.; "Nitric Oxide-Releasing Compounds: From Basic Research to Promising Drugs"; Chemtech; Aug. 1998; pp. 30-35 (pp. 1-8); vol. 28, No. 8; located at: http://pubs.acs.org/hotartcl/chemtech/98/aug/nitric.html; printed on Oct. 2, 2007; The American Chemical Society.
Khan, MA et al.; "The Effect of Superoxide Dismutase on Nitric Oxide-Mediated and Electrical Field-Stimulated Diabetic Rabbit Cavernosal Smooth Muscle Relaxation"; BJU Int.; Jan. 2001; pp. 98-103 (p. 1); vol. 87, No. 1; located at: http://www.pubmed.gov; printed on Sep. 27, 2007 (Abstract Only).
Kim, SC et al.; "Effects of Ultraviolet Light on the Tension of Isolated Human Cavernosal Smooth Muscle from Non-Diabetic and Diabetic Impotent Men"; Urol. Res.; 1997; pp. 149-152 (p. 1); vol. 25, No. 2; located at: http://www.pubmed.gov; printed on Sep. 27, 2007 (Abstract Only).
Kim, JH et al; "Mechanism of UV Light-Induced Photorelaxation in Isolated Rat Aorta"; J. Vet. Sci.; Dec. 2000; pp. 81-86 (p. 1); vol. 1, No. 2; located at: http://www.pubmed.gov; printed on Oct. 26, 2007 (Abstract Only).
"Light-Emitting Diode (LED)"; Fiber Optics; Bearing a date of 2005; pp. 1-10; located at: http://www.fiber-optics.info/articles/LEDs.htm; printed on Oct. 6, 2007.
Matthews, EK et al.; "Photon Pharmacology of an Iron-Sulphur Cluster Nitrosyl Compound Acting on Smooth Muscle"; Br. J. Pharmacol.; Sep. 1994; pp. 87-94 (p. 1); vol. 113, No. 1; located at: http://www.pubmed.gov; printed on Oct. 26, 2007 (Abstract Only) .
Mendioroz, A. et al.; "Infrared to Visible and Ultraviolet Upconversion Processes in Nd$^{3+}$-Doped Potassium Lead Chloride Crystal"; Optical Materials; Sep. 2004; pp. 351-357 (p. 1); vol. 26, Issue 4; located at: http://www.sciencedirect.com; printed on Oct. 29, 2007 (Abstract Only).
Nablo, Brian J. et al.; "Inhibition of Implant-Associated Infections Via Nitric Oxide Release"; Biomaterials; Dec. 2005; pp. 6984-6990 (p. 1); vol. 26, Issue 34; located at: http://www.sciencedirect.com; printed on Oct. 26, 2007 (Abstract Only).
"Particulate Effects on Immunologic Function"; OST 1997AR; Bearing a date of 1997; pp. 1-2; located at: http://www.fda.gov/cdrh/ost/rpt97/OST1997AR9.HTML; printed on Oct. 16, 2007.
Peng, H. et al.; "Ultraviolet Light-Emitting Diodes Operating in the 340 nm Wavelength Range and Application to Time-Resolved Fluorescence Spectroscopy"; Applied Physics Letters; Aug. 23, 2004; pp. 1436-1438 (p. 1); vol. 85, Issue 8; located at: http://scitation.aip.org; printed on Oct. 26, 2007 (Abstract Only).
Pou, SJ et al.; "Biological Studies of a Nitroso Compound that Releases Nitric Oxide Upon Illumination"; Molecular Pharmacology; Oct. 1, 1994; pp. 709-715 (p. 1); Vo. 46, Issue 4; located at: http://molpharm.aspetjournals.org/cgi/content/abstract/46/4/709; printed on Oct. 26, 2007 (Abstract Only).
Rotta, J.C.G. et al.; "Nitric Oxide Release from the S-Nitrosothiol Zinc Phthalocyanine Complex by Flash Photolysis"; Brazilian Journal of Medical and Biological Research; 2003; pp. 587-594; vol. 36, No. 5; located at: http://www.scielo.br/pdf/bjmbr/v36n5/4604.pdf.
Seo, K.K. et al.; "Synergistic Effects of Sildenafil on Relaxation of Rabbit and Rat Cavernosal Smooth Muscles when Combined with Various Vasoactive Agents"; BJU International; 2001; pp. 596-601; vol. 88.
Singh, Ravinder Jit et al.; "Photosensitized Decomposition of S-Nitrosothiols and 2-Methyl-2-Nitrosopropane Possible Use for Site-Directed Nitric Oxide Production"; FEBS Letters; 1995; pp. 47-51; vol. 360; Federation of European Biochemical Societies.
Smith, DJ et al.; "Nitric Oxide-Releasing Polymers Containing the [N(O)NO]-Group"; J. Med. Chem.; Mar. 1, 1996; pp. 1148-1156 (p. 1); vol. 39, No. 5; located at: http://www.pubmed.gov; printed on Oct. 26, 2007 (Abstract Only).
Wadsworth, Roger et al.; "Physiologically Relevant Measurements of Nitric Oxide in Cardiovascular Research Using Electrochemical Microsensors"; Journal of Vascular Research; 2006; pp. 70-85; vol. 43; S. Karger AG, Basel.
Wang, Peng George et al.; "Nitric Oxide Donors: Chemical Activities and Biological Applications"; Chem. Rev.; 2002; pp. 1091-1134 (pp. 1-53); vol. 102, No. 4; American Chemical Society; located at: http://pubs.acs.org/cgi-bin/abstract.cgi/chreay/2002/102/i04/abs/cr0000401.html; printed on Oct. 26, 2007.
Wang, Tianlong et al.; "Inhaled Nitric Oxide in 2003: A Review of its Mechanisms of Action"; Canadian Journal of Anesthesia; 2003; pp. 839-846; vol. 50, No. 8.
Williamson, David; "Study: Nitric Oxide-Releasing Materials Might Reduce Medical Implant Infections"; UNC News Services; Sep. 7, 2001; pp. 1-2; No. 416; located at: http://www.unc.edu/news/archives/sep01/schoen090701.htm; printed on Oct. 4, 2007.
Xie, Rong-Jun; "Highly Efficient White-Light-Emitting Diodes Fabricated with Short-Wavelength Yellow Oxynitride Phosphors"; Applied Physics Letters; Mar. 6, 2006; pp. 101104.1-101104.3 (pp. 1-2); vol. 88; located at: http://scitation.aip.org/; printed on Oct. 26, 2007 (Abstract Only).
Jamal, Sophie A. et al.; "Effect of Nitroglycerin Ointment on Bone Density and Strength in Postmenopausal Women"; JAMA; bearing a date of Feb. 23, 2011; pp. 800-807; vol. 305, No. 8; American Medical Association.
Khosla, Sundeep; "Is Nitroglycerin a Novel and Inexpensive Treatment for Osteoporosis?"; JAMA; bearing a date of Feb. 23, 2011; pp. 826-827; vol. 305, No. 8; American Medical Association.
Mims, Christopher; "Erectile Dysfunction Treatment to Save Soldiers' Lives"; Technology Review; bearing a date of Feb. 22, 2011; 2 pages; MIT; located at http://www.technologyreview.com/blog/mimssbits/26427/?pl=A5.
U.S. Appl. No. 12/930,351, Hyde et al.
Liu et al.; "Novel Delivery System for the Bioregulatory Agent Nitric Oxide"; Chemistry of Materials; bearing a date of 2009; pp. 5032-5041; vol. 21, No. 21; © 2009 American Chemical Society.

(56) References Cited

OTHER PUBLICATIONS

"Nitric oxide-releasing wrap for donor organs and cloth for therapeutic socks"; e! Science News; bearing a date of Jan. 6, 2010; pp. 1-2; located at http://esciencenews.com/articles/2010/01/06/nitric.oxide.releasing.wrap.donor.organs.and.cloth.therapeutic.socks; printed on Jan. 19, 2010.

Birkeland et al.; "On the Oxidation of Atmospheric Nitrogen in Electric Arcs"; Nature; bearing a date of 1898; pp. 98-116; No. 1,506, vol. 58.

Levine et al.; "A New, Highly Efficient Red-Emitting Cathodoluminescent Phosphor ($YVO_4$:Eu) for Color Television"; Applied Physics Letters; bearing a date of Sep. 15, 1964; pp. 1-3; vol. 5, No. 6.

Mellor, J. W.; "Modern Inorganic Chemistry"; excerpt from Modern Inorganic Chemistry; bearing a date of 1912; pp. 1-19; Longmans, Greene, and Co.

"The Shadow Mask and Aperture Grill"; The PC Guide; bearing a date of Apr. 17, 2001; pp. 1-3; © Copyright 1997-2004 Charles M. Kozierok; printed Oct. 6, 2009; located at http://www.pcguide.com/ref/crt/crtMask-c.html.

U.S. Appl. No. 12/928,029, Hyde et al.
U.S. Appl. No. 12/928,028, Hyde et al.
U.S. Appl. No. 12/927,610, Hyde et al.
U.S. Appl. No. 12/008,708, Hyde et al.
U.S. Appl. No. 12/008,694, Hyde et al.
U.S. Appl. No. 12/006,090, Hyde et al.
U.S. Appl. No. 12/006,069, Hyde et al.
U.S. Appl. No. 12/006,049, Hyde et al.
U.S. Appl. No. 12/005,170, Hyde et al.
U.S. Appl. No. 12/005,136, Hyde et al.
U.S. Appl. No. 12/005,132, Hyde et al.
U.S. Appl. No. 12/005,065, Hyde et al.
U.S. Appl. No. 12/005,045, Hyde et al.
U.S. Appl. No. 11/998,864, Roderick A. Hyde.

Burrell, María A. et al.; "Detection of Nitric Oxide Synthase (NOS) in Somatostatin-Producing Cells of Human and Murine Stomach and Pancreas"; The Journal of Histochemistry and Cytochemistry; 1996; pp. 339-346; vol. 44, No. 4; The Histochemical Society, Inc.

Gau, Jen-JR et al.; "A MEMS Based Amperometric Detector for E. coli Bacteria Using Self-Assembled Monolayers"; Biosensors & Bioelectronics; 2001; pp. 745-755; vol. 16; Elsevier Science B.V.

Graham-Rowe, Duncan; "Photonic Fabrics Take Shape"; Nature Photonics; Jan. 2007; pp. 6-7; vol. 1; Nature Publishing Group.

Hattenbach, Lars-Olof et al.; "Detection of Inducible Nitric Oxide Synthase and Vascular Endothelial Growth Factor in Choroidal Neovascular Membranes"; Ophthalmologica; 2002; pp. 209-214; vol. 216; S. Karger AG, Basel.

Hou, Yongchun et al.; "Nanomolar Scale Nitric Oxide Generation from Self-Assembled Monolayer Modified Gold Electrodes"; Chem. Commun.; 2000; pp. 1831-1832; The Royal Society of Chemistry.

Hrabie, Joseph A.; Keefer, Larry K.; "Chemistry of the Nitric Oxide-Releasing Diazeniumdiolate ("Nitrosohydroxylamine") Functional Group and Its Oxygen-Substituted Derivatives"; Chem. Rev.; 2002; pp. 1135-1154; vol. 102; American Chemical Society.

Ikeda, Osamu et al.; "Nitric Oxide Detection with Glassy Carbon Electrodes Coated with Charge-Different Polymer Films"; Sensors; Apr. 26, 2005; pp. 161-170; vol. 5; ISSN 1424-8220; MDPI.

Li, Chang Ming et al.; "Electrochemical Detection of Nitric Oxide on a SWCNT/RTIL Composite Gel Microelectrode"; Electroanalysis; 2006; pp. 713-718; vol. 18, No. 7; Wiley-VCH Verlag GmbH & Co. KGaA, Weinheim.

Lin, Hong-Yu et al.; "Side-Polished Multimode Fiber Biosensor Based on Surface Plasmon Resonance with Halogen Light"; Applied Optics; Feb. 10, 2007; pp. 800-806; vol. 46, No. 5; Optical Society of America.

"NO Electrodes"; WPI-Europe-Biosensing-NO Electrodes; Bearing a date of Nov. 29, 2007; pp. 1-5; World Precision Instruments; located at: http://www.wpi-europe.com/products/biosensing/noelectrodes.htm; printed on Nov. 29, 2007.

"Probes for Nitric Oxide (NO) Research"; EMD-Calbiochem: Nitric Oxide Probes; Bearing a date of 2007; pp. 1-2; Calbiochem, Novabiochem, & Novagen; located at: http://www.emdbiosciences.com/html/cbc/nitric_oxide_probes.htm; printed on Nov. 29, 2007.

Räthel, Thomas R. et al.; "Application of 4,5-Diaminofluorescein to Reliably Measure Nitric Oxide Released from Endothelial Cells In Vitro"; Biological Procedures Online; Jun. 2, 2003; pp. 136-142; vol. 5, No. 1.

Sonoki, T. et al.; "Detection of Inducible Nitric Oxide Synthase (iNOS) mRNA by RT-PCR in ATL Patients and HTLV-1 Infected Cell Lines: Clinical Features and Apoptosis by NOS Inhibitor"; Leukemia; 1999; pp. 713-718; vol. 13; Stockton Press.

Dictionary.com; "Patch"; printed on Jul. 20, 2012; pp. 1-8; located at: http://dictionary.reference.com/browse/patch.

U.S. Appl. No. 13/452,502, Hyde et al.

Walt et al.; "Biological Warfare"; Analytical Chemistry; Dec. 1, 2000; pp. 738 A-747 A.

"Nanotechnology—the new Viagra?"; Nanowerk News; bearing a date of Apr. 26, 2009; p. 1; located at http://www.nanowerk.com/news/newsid=10273.php.

* cited by examiner

700 A system comprising:
702 a signal-bearing medium bearing
704 one or more instructions for presenting information about use of one or more photolyzable nitric oxide donors for treatment of sexual dysfunction
706 a computer-readable medium
708 a recordable medium
710 a communications medium 800 A system comprising:
802 a signal-bearing medium bearing
804 one or more instructions for presenting information about use of one or more light sources that are configured to facilitate release of nitric oxide for treatment of sexual dysfunction
806 a computer-readable medium
808 a recordable medium
810 a communications medium

METHODS AND SYSTEMS FOR USE OF PHOTOLYZABLE NITRIC OXIDE DONORS

TECHNICAL FIELD

The present disclosure relates to methods and systems for use of photolyzable nitric oxide donors for the treatment of sexual dysfunction.

SUMMARY

In some embodiments one or more methods for treating sexual dysfunction are provided that include administering one or more photolyzable nitric oxide donors to an individual and illuminating the individual with light that facilitates release of nitric oxide from the one or more photolyzable nitric oxide donors to treat the sexual dysfunction. In addition to the foregoing, other aspects are described in the claims, drawings, and text forming a part of the present disclosure.

In some embodiments one or more systems are provided that include circuitry for administering one or more photolyzable nitric oxide donors to an individual and circuitry for illuminating the individual with light that facilitates release of nitric oxide from the one or more photolyzable nitric oxide donors to treat sexual dysfunction. In addition to the foregoing, other aspects are described in the claims, drawings, and text forming a part of the present disclosure.

In some embodiments one or more systems for treating sexual dysfunction are provided that include means for administering one or more photolyzable nitric oxide donors to an individual and means for illuminating the individual with light that facilitates release of nitric oxide from the one or more photolyzable nitric oxide donors to treat the sexual dysfunction. In addition to the foregoing, other aspects are described in the claims, drawings, and text forming a part of the present disclosure.

In some embodiments one or more systems are provided that include a signal-bearing medium bearing one or more instructions for administering one or more photolyzable nitric oxide donors to an individual and one or more instructions for illuminating the individual with light that facilitates release of nitric oxide from the one or more photolyzable nitric oxide donors to treat sexual dysfunction. In addition to the foregoing, other aspects are described in the claims, drawings, and text forming a part of the present disclosure.

In some embodiments one or more systems are provided that include a signal-bearing medium bearing one or more instructions for presenting information about use of one or more photolyzable nitric oxide donors for treatment of sexual dysfunction. In addition to the foregoing, other aspects are described in the claims, drawings, and text forming a part of the present disclosure.

In some embodiments one or more systems are provided that include a signal-bearing medium bearing one or more instructions for presenting information about use of one or more light sources that are configured to facilitate release of nitric oxide for treatment of sexual dysfunction. In addition to the foregoing, other aspects are described in the claims, drawings, and text forming a part of the present disclosure.

In some embodiments, means include but are not limited to circuitry and/or programming for effecting the herein referenced functional aspects; the circuitry and/or programming can be virtually any combination of hardware, software, and/or firmware configured to effect the herein referenced functional aspects depending upon the design choices of the system designer. In addition to the foregoing, other system aspects means are described in the claims, drawings, and/or text forming a part of the present disclosure.

In some embodiments, related systems include but are not limited to circuitry and/or programming for effecting the herein referenced method aspects; the circuitry and/or programming can be virtually any combination of hardware, software, and/or firmware configured to effect the herein referenced method aspects depending upon the design choices of the system designer. In addition to the foregoing, other system aspects are described in the claims, drawings, and/or text forming a part of the present application.

The foregoing summary is illustrative only and is not intended to be in any way limiting. In addition to the illustrative aspects, embodiments, and features described above, further aspects, embodiments, and features will become apparent by reference to the drawings, claims, and the following detailed description.

DETAILED DESCRIPTION

Figure 1:
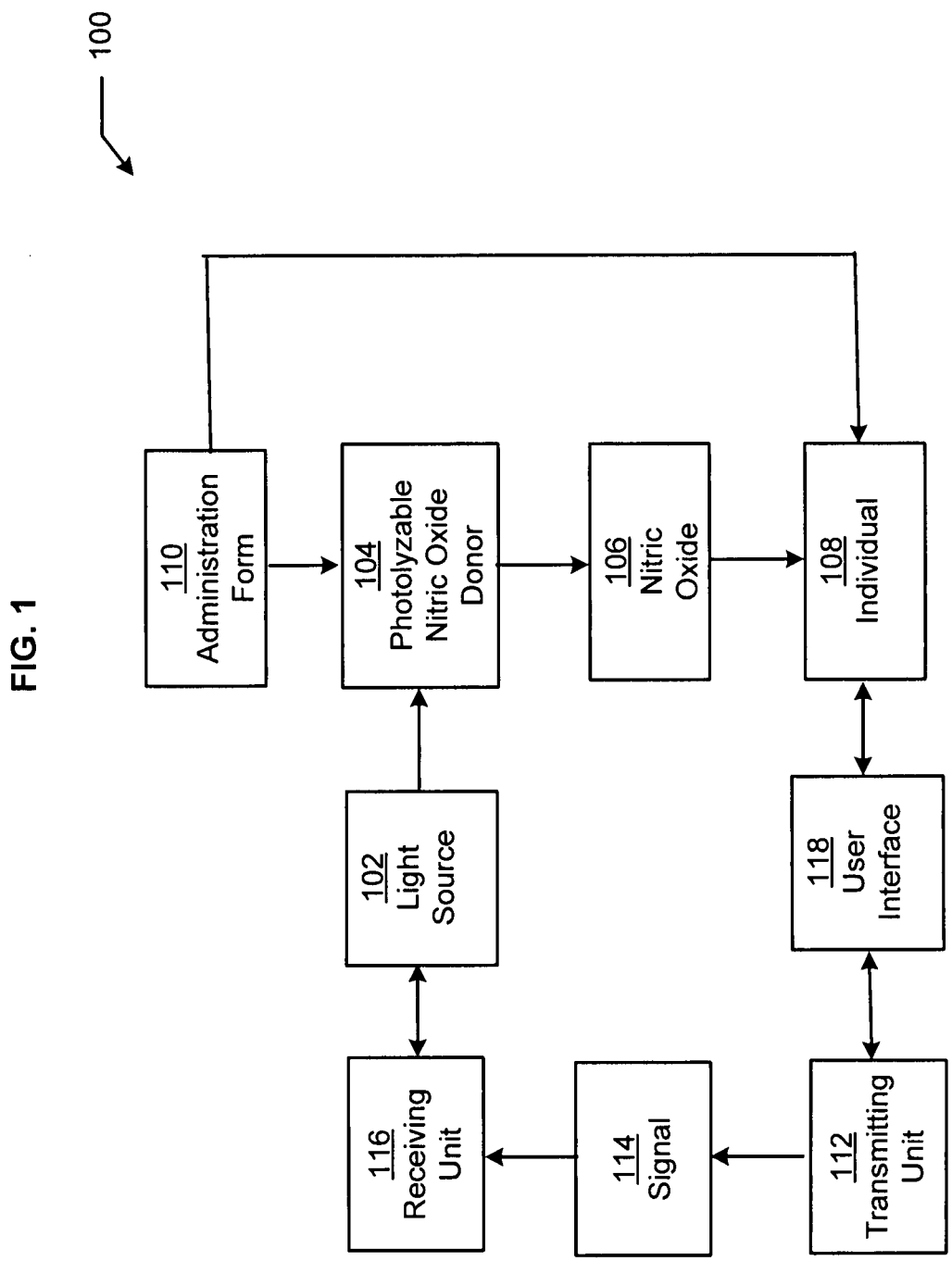
FIG. 1 illustrates an example system 100 in which embodiments may be implemented.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

FIG. 1 illustrates an example system 100 in which embodiments may be implemented. In some embodiments, one or more photolyzable nitric oxide donors 104 may be administered to one or more individuals 108 through use of one or more administration forms 110. Such photolyzable nitric oxide donors 104 may be used to administer nitric oxide 106 to one or more individuals 108. In some embodiments, one or more transmitting units 112 may be used to transmit one or more signals 114 to one or more receiving units 116. In some embodiments, an individual 108 to whom nitric oxide 106 is being administered may control the one or more transmitting units 112. In some embodiments, a person other than the individual 108 to whom nitric oxide 106 is being administered may control the one or more transmitting units 112. In some embodiments, one or more receiving units 116 may be associated with one or more light sources 102. Accordingly, in some embodiments, one or more signals 114 may include information that may be used to control the one or more light sources 102.

Light Source

Numerous light sources 102 may be used within system 100. In some embodiments, one or more light sources 102 may be used to facilitate release of nitric oxide 106 from one or more photolyzable nitric oxide donors 104. In some embodiments, one or more light sources 102 may be configured to emit light of multiple wavelengths. In some embodiments, one or more light sources 102 may be configured to emit light that is selected to facilitate release of nitric oxide 106 from one or more photolyzable nitric oxide donors 104. For example, in some embodiments, one or more light sources 102 may be configured to emit one or more wavelengths of light that are selected to facilitate release of nitric oxide 106 from one or more identified photolyzable nitric oxide donors 104. In some embodiments, one or more light sources 102 may emit one or more wavelengths of light that are selected based on the absorption spectrum of one or more photolyzable nitric oxide donors 104. In some embodiments, one or more light sources 102 may emit one or more wavelengths of light that are selected based on decomposition of one or more photolyzable nitric oxide donors 104. For example, in some embodiments, one or more light sources 102 may be configured to emit one or more wavelengths of light that cause decomposition of one or more photolyzable nitric oxide donors 104 without causing injury to adjacent structures and/or tissues. In some embodiments, a first light source 102 may be configured to emit one or more wavelengths of light that cause a first photolyzable nitric oxide donor 104 to release nitric oxide 106 and a second light source 102 may be configured to emit one or more wavelengths of light that cause a second photolyzable nitric oxide donor 104 to release nitric oxide 106. Accordingly, numerous light sources 102 may be coupled with numerous types of photolyzable nitric oxide donors 104 to provide for selective release of nitric oxide 106.

In some embodiments, one or more light sources 102 may include one or more quantum dots (e.g., U.S. Pat. No. 7,235,361; herein incorporated by reference). For example, in some embodiments, one or more light sources 102 may be configured to emit one or more wavelengths of light that are absorbed by one or more quantum dots. In some embodiments, one or more quantum dots may be configured to absorb light and then emit one or more wavelengths of light that cause release of nitric oxide 106 from one or more nitric oxide donors 104. Accordingly, in some embodiments, emission from one or more first quantum dots may be tuned to facilitate release of nitric oxide 106 from one or more first photolyzable nitric oxide donors 104 and emission from one or more second quantum dots may be tuned to facilitate release of nitric oxide 106 from one or more second photolyzable nitric oxide donors 104.

In some embodiments, one or more light sources 102 may be configured to be used internally to illuminate one or more regions of an individual 108. A light source 102 may be configured in numerous ways. For example, in some embodiments, one or more light sources 102 may be configured for insertion into the urethra of a male and/or a female (e.g., U.S. Pat. No. 4,248,214; herein incorporated by reference). In some embodiments, one or more light sources 102 may be configured for vaginal insertion into a female. In some embodiments, one or more light sources 102 may be configured for implantation into an individual 108. For example, in some embodiments, one or more light sources 102 may be configured for implantation into the genital region of a male and/or a female. For example, in some embodiments, one or more light sources 102 may be configured for implantation within the corpus cavernosa of a penis. In some embodiments, one or more light sources 102 may be configured for implantation into the scrotal sack of a male. For example, in some embodiments, one or more light sources 102 may be configured to include one or more energy sources (e.g., one or more batteries), one or more light emitters (e.g., one or more light emitting diodes), and one or more optical fibers to deliver light to a selected region of an individual 108. In some embodiments, such light sources 102 may be implanted such that the energy sources and the light emitters are implanted into the scrotal sack of a male and optical fibers may be operably coupled to the one or more light emitters and implanted within the corpus cavernosa of the associated penis.

In some embodiments, one or more light sources 102 may be configured to externally illuminate an individual 108. Accordingly, one or more light sources 102 may be configured in numerous ways. For example, in some embodiments, a light source 102 may be configured as a lamp, a flashlight, a wand, a ring, a glove, a sheet, a condom, and the like. In some embodiments, one or more light sources 102 may be included within clothing.

In some embodiments, light sources 102 may be remotely controlled. For example, in some embodiments, one or more light sources 102 may be configured to receive one or more signals 114 that include instructions for operation of the one or more light sources 102. Such instructions may be associated with emission of light, non-emission of light, time when light is emitted, length of light emission, intensity of light emission, wavelengths of emitted light, and the like.

In some embodiments, light sources 102 may be configured to include one or more control units. In some embodiments, one or more light sources 102 may be configured to include a switch that may be used to turn the light source 102 on and off. For example, in some embodiments, a light source 102 may be configured to include a push button switch to turn the light source 102 on and off.

In some embodiments, one or more light sources 102 may include one or more light emitters that are coupled to one or more electromagnetic receivers. The one or more electromagnetic receivers may be configured to couple with one or more electromagnetic transmitters that produce one or more electromagnetic fields that induce an electrical current to flow in the one or more electromagnetic receivers to energize the light emitters (e.g., U.S. Pat. No. 5,571,152; herein incorporated by reference). Accordingly, in some embodiments, one or more light sources 102 may be configured such that they are not directly coupled to an energy source.

A light source 102 may be configured to emit numerous types of light. In some embodiments, emitted light may be visible light. In some embodiments, emitted light may be infrared light. In some embodiments, emitted light may be ultraviolet light. In some embodiments, emitted light may be substantially any combination of visible light, infrared light, and/or ultraviolet light. In some embodiments, one or more light sources 102 may emit fluorescent light. In some embodiments, one or more light sources 102 may emit phosphorescent light.

In some embodiments, one or more light sources 102 may be configured to emit light continuously. In some embodiments, one or more light sources 102 may be configured to emit light as a pulse. In some embodiments, one or more light sources 102 may be configured to emit light as a flash. In some embodiments, one or more light sources 102 may be configured to emit light continuously, as a pulse, as a flash, or substantially any combination thereof.

In some embodiments, one or more light emitters and/or light sources 102 may be configured to provide for upconversion of energy. In some embodiments, infrared light may be upconverted to visible light (e.g., Mendioroz et al., Optical Materials, 26:351-357 (2004). In some embodiments, infrared light may be upconverted to ultraviolet light (e.g., Mendioroz et al., Optical Materials, 26:351-357 (2004). In some embodiments, one or more light sources 102 may include one or more rare-earth materials (e.g., ytterbium-erbium, ytterbium-thulium, or the like) that facilitate upconversion of energy (e.g., U.S. Pat. No. 7,088,040; herein incorporated by reference). For example, in some embodiments, one or more light sources 102 may be associated with $Nd^{3+}$ doped $KPb_2Cl_5$ crystals. In some embodiments, one or more light sources 102 may be associated with thiogallates doped with rare earths, such as $CaGa_2S_4:Ce^{3+}$ and $SrGa_2S_4:Ce^{3+}$. In some embodiments, one or more light sources 102 may be associated with aluminates that are doped with rare earths, such as $YAlO_3:Ce^{3+}$, $YGaO_3:Ce^{3+}$, $Y(Al,Ga)O_3:Ce^{3+}$, and orthosilicates $M_2SiO_5:Ce^{3+}$ (M:Sc, Y, Sc) doped with rare earths, such as, for example, $Y_2SiO_5:Ce^{3+}$. In some embodiments, yttrium may be replaced by scandium or lanthanum (e.g., U.S. Pat. Nos. 6,812,500 and 6,327,074; herein incorporated by reference). Numerous materials that may be used to upconvert energy have been described (e.g., U.S. Pat. Nos. 5,956,172; 5,943,160; 7,235,189; 7,215,687; herein incorporated by reference).

Photolyzable Nitric Oxide Donor/Nitric Oxide

Numerous photolyzable nitric oxide donors 104 may be used within system 100. Examples of such photolyzable nitric oxide donors 104 include, but are not limited to, diazeniumdiolates (e.g., U.S. Pat. Nos. 7,105,502; 7,122,529; 6,673,338; herein incorporated by reference), trans-[RuCl([15]aneN4)NO]+2 (Ferezin et al., Nitric Oxide, 13:170-175 (2005), Bonaventura et al., Nitric Oxide, 10:83-91 (2004)), nitrosyl ligands (e.g., U.S. Pat. No. 5,665,077; herein incorporated by reference, Chmura et al., Nitric Oxide, 15:370-379 (2005), Flitney et al., Br. J. Pharmacol., 107:842-848 (1992), Flitney et al., Br. J. Pharmacol., 117:1549-1557 (1996), Matthews et al., Br. J. Pharmacol., 113:87-94 (1994)), 6-Nitrobenzo[a]pyrene (e.g., Fukuhara et al., J. Am. Chem. Soc., 123:8662-8666 (2001)), S-nitroso-glutathione (e.g., Rotta et al., Braz. J. Med. Res., 36:587-594 (2003), Flitney and Megson, J. Physiol., 550:819-828 (2003)), S-nitrosothiols (e.g., Andrews et al., British Journal of Pharmacology, 138:932-940 (2003), Singh et al., FEBS Lett., 360:47-51 (1995)), 2-Methyl-2-nitrosopropane (e.g., Pou et al., Mol. Pharm., 46:709-715 (1994), Wang et al., Chem. Rev., 102:1091-1134 (2002)), imidazolyl derivatives (e.g., U.S. Pat. No. 5,374,710; herein incorporated by reference).

In some embodiments, one or more photolyzable nitric oxide donors 104 may be used in association with additional nitric oxide donors that are not photolyzable. In some embodiments, one or more photolyzable nitric oxide donors 104 may be used in association with additional agents. Examples of such additional agents include, but are not limited to, enzyme inhibitors (e.g., U.S. Pat. No. 6,943,166; herein incorporated by reference), agents that increase the effects and/or concentration of nitric oxide 106 (e.g., methylene blue and N(w)-nitro-L-arginine (L-NOARG) (see Chen and Gillis, Biochem. Biophys. Res. Commun., 190, 559-563 (1993) and Kim et al., J. Vet. Sci., 1:81-86 (2000)), L-arginine (e.g., U.S. Published Patent Application No. 20020068365 and U.S. Pat. No. 6,635,273; herein incorporated by reference), agents that stabilize nitric oxide donors (e.g., dimethyl sulfoxide and ethanol), agents that increase the half life of nitric oxide 106 (e.g., U.S. Published Patent Application No. 20030039697; herein incorporated by reference), and the like.

Individual

Photolyzable nitric oxide donors 104 may be used to treat numerous types of individuals 108 for sexual dysfunction (e.g., human individuals 108). In some embodiments, one or more photolyzable nitric oxide donors 104 may be used to treat female arousal disorder. In some embodiments, one or more photolyzable nitric oxide donors 104 may be used to treat male erectile disorder. In some embodiments, sexual dysfunction may be due to a physical condition. For example, in some embodiments, sexual dysfunction may result from surgery, a physical injury, pharmaceutical use, age, or the like. In some embodiments, sexual dysfunction may be due to a mental condition. For example, in some embodiments, sexual dysfunction may be due to depression, lack of interest, insecurity, anxiety, or the like. In some embodiments, one or more photolyzable nitric oxide donors 104 may be used to increase sexual performance and/or pleasure.

Administration Form

Numerous types of administration forms 110 may be used to provide one or more photolyzable nitric oxide donors 104 to an individual 108. In some embodiments, an administration form 110 may be a formulation of one or more photolyzable nitric oxide donors 104. In some embodiments, an administration form 110 may be configured for oral delivery of one or more photolyzable nitric oxide donors 104 to an individual 108. For example, in some embodiments, an administration form 110 may be configured as a pill, a lozenge, a capsule, a liquid, and the like. In some embodiments, an administration form 110 may be configured for topical delivery of one or more photolyzable nitric oxide donors 104 to an individual 108. For example, in some embodiments, an administration form 110 may be configured as a gel, a cream, a lotion, a lubricant, a jelly, and the like. In some embodiments, one or more photolyzable nitric oxide donors 104 may be formulated with one or more liposomes to provide for delivery of the one or more photolyzable nitric oxide donors 104 to the individual 108. In some embodiments, one or more photolyzable nitric oxide donors 104 may be formulated with one or more detergents to facilitate delivery of the one or more photolyzable nitric oxide donors 104 to the individual 108. In some embodiments, one or more photolyzable nitric oxide donors 104 may be formulated with one or more agents that stabilize the one or more photolyzable nitric oxide donors 104. In some embodiments, one or more photolyzable nitric oxide donors 104 may be formulated for administration to one or more individuals 108 through inhalation. In some embodiments, one or more photolyzable nitric oxide donors 104 may be formulated for administration to one or more individuals 108 through parenteral administration.

In some embodiments, an administration form 110 may include an implant. In some embodiments, one or more photolyzable nitric oxide donors 104 may be coupled to a structure that can be implanted within an individual 108. For example, in some embodiments, one or more photolyzable nitric oxide donors 104 may be coupled to a polymeric structure for implantation into an individual 108 (e.g., U.S. Pat. Nos. 5,405,919; 6,451,337; 7,052,711: herein incorporated by reference, Smith et al., J. Med. Chem., 1:1148-1156 (1996)). In some embodiments, one or more photolyzable nitric oxide donors 104 may be included within a porous structure and/or matrix for implantation into an individual 108 (e.g., U.S. Published Patent Application No. 20030039697; herein incorporated by reference). Such structures may be constructed from numerous materials that include, but are not limited to, polymers, ceramics, metals, and the like. In some embodiments, one or more photolyzable nitric oxide donors 104 may be formulated for depot administration to an individual 108. For example, in some embodiments, one or more photolyzable nitric oxide donors 104 may be formulated with one or more biodegradable materials that degrade within an individual 108 to release the one or more photolyzable nitric oxide donors 104 (e.g., U.S. Pat. Nos. 5,736,152; 6,143,314; 6,773,714; herein incorporated by reference). Accordingly, in some embodiments, one or more photolyzable nitric oxide donors 104 may be included within a flowable material that forms an implant upon being injected into an individual 108.

In some embodiments, one or more photolyzable nitric oxide donors 104 may be formulated with one or more additional agents. Examples of such agents include, but are not limited to, enzyme inhibitors, additional nitric oxide donors, free radical scavengers, and the like. In some embodiments, one or more photolyzable nitric oxide donors 104 may be formulated with one or more light sources 102 (e.g., U.S. Pat. No. 5,571,152; herein incorporated by reference). In some embodiments, one or more photolyzable nitric oxide donors 104 may be formulated with one or more quantum dots (e.g., U.S. Pat. No. 7,235,361; herein incorporated by reference).

Transmitting Unit

The system 100 may include one or more transmitting units 112. Numerous types of transmitting units 112 may be used in association with system 100. Examples of such transmitting units 112 include, but are not limited to, transmitters that transmit one or more optical signals 114, radio signals 114, wireless signals 114, hardwired signals 114, infrared signals 114, ultrasonic signals 114, and the like (e.g., U.S. Pat. Nos. RE39,785; 7,260,768; 7,260,764; 7,260,402; 7,257,327; 7,215,887; 7,218,900; herein incorporated by reference). In some embodiments, one or more transmitting units 112 may transmit one or more signals 114 that are encrypted. Numerous types of transmitters are known and have been described (e.g., U.S. Pat. Nos. and Published U.S. Pat. Nos. 7,236,595; 7,260,155; 7,227,956; US2006/0280307; herein incorporated by reference).

Signal

Numerous types of signals 114 may be used in association with system 100. Examples of such signals 114 include, but are not limited to, optical signals 114, radio signals 114, wireless signals 114, hardwired signals 114, infrared signals 114, ultrasonic signals 114, and the like.

In some embodiments, one or more signals 114 may not be encrypted. In some embodiments, one or more signals 114 may be encryped. In some embodiments, one or more signals 114 may be sent through use of a secure mode of transmission. In some embodiments, one or more signals 114 may be coded for receipt by a specific individual 108. In some embodiments, such code may include anonymous code that is specific for an individual 108. Accordingly, information included within one or more signals 114 may be protected against being accessed by others who are not the intended recipient.

Receiving Unit

The system 100 may include one or more receiving units 116. Numerous types of receiving units 116 may be used in association with system 100. Examples of such receiving units 116 include, but are not limited to, receivers that receive one or more optical signals 114, radio signals 114, wireless signals 114, hardwired signals 114, infrared signals 114, ultrasonic signals 114, and the like. Such receivers are known and have been described (e.g., U.S. Pat. Nos. RE39,785; 7,218,900; 7,254,160; 7,245,894; 7,206,605; herein incorporated by reference).

User Interface/User

System 100 may include numerous types of user interfaces 118. For example, one or more users (e.g., individuals 108) may interact through use of numerous user interfaces 118 that utilize hardwired methods, such as through use of an on/off switch or push button, use of wireless methods, such as use of a transmitter and receiver, and the like.

Figure 2:
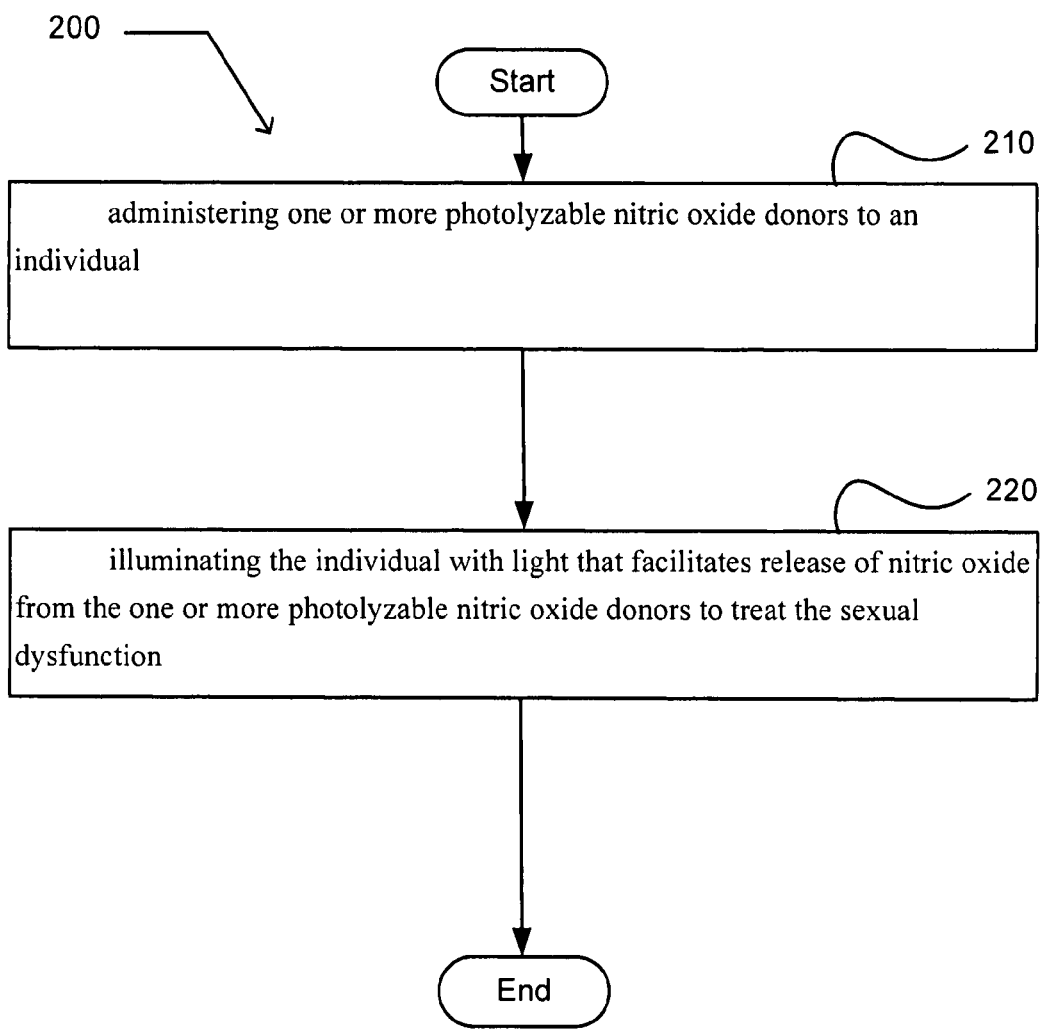
FIG. 2 illustrates an operational flow representing example operations related to methods and systems associated with the treatment of sexual dysfunction.

FIG. 2 illustrates an operational flow 200 representing examples of operations that are related to the performance of a method for using photolyzable nitric oxide donors 104 for the treatment of sexual dysfunction. In FIG. 2 and in following figures that include various examples of operations used during performance of the method, discussion and explanation may be provided with respect to any one or combination of the above-described examples of FIG. 1, and/or with respect to other examples and contexts. However, it should be understood that the operations may be executed in a number of other environments and contexts, and/or modified versions of FIG. 1. Also, although the various operations are presented in the sequence(s) illustrated, it should be understood that the various operations may be performed in other orders than those which are illustrated, or may be performed concurrently.

After a start operation, the operational flow 200 includes an administering operation 210 involving administering one or more photolyzable nitric oxide donors to an individual. In some embodiments, one or more administration forms 110 may be used to administer one or more photolyzable nitric oxide donors 104 to an individual 108.

After a start operation, the operational flow 200 includes an illuminating operation 220 involving illuminating the individual with light that facilitates release of nitric oxide from the one or more photolyzable nitric oxide donors to treat the sexual dysfunction. In some embodiments, one or more light sources 102 may be used to illuminate the individual 108 with light that facilitates release of nitric oxide 106 from the one or more photolyzable nitric oxide donors 104 to treat the sexual dysfunction. In some embodiments, treating sexual dysfunction includes, but is not limited to treating male erectile dysfunction. Treating male erectile dysfunction may include, but is not limited to, facilitating the achievement of a penile erection, increasing the rigidity of a penile erection, increasing blood flow to the penis, increasing the duration of a penile erection, or substantially any combination thereof. In some embodiments, treating sexual dysfunction includes, but is not limited to treating female arousal disorder. Treating female arousal disorder may include, but is not limited to, increasing blood flood to the genitalia of a female (e.g., vagina, clitoris, etc.), increasing vaginal lubrication, increasing clitoral vasocongestion, and the like.

Figure 3:
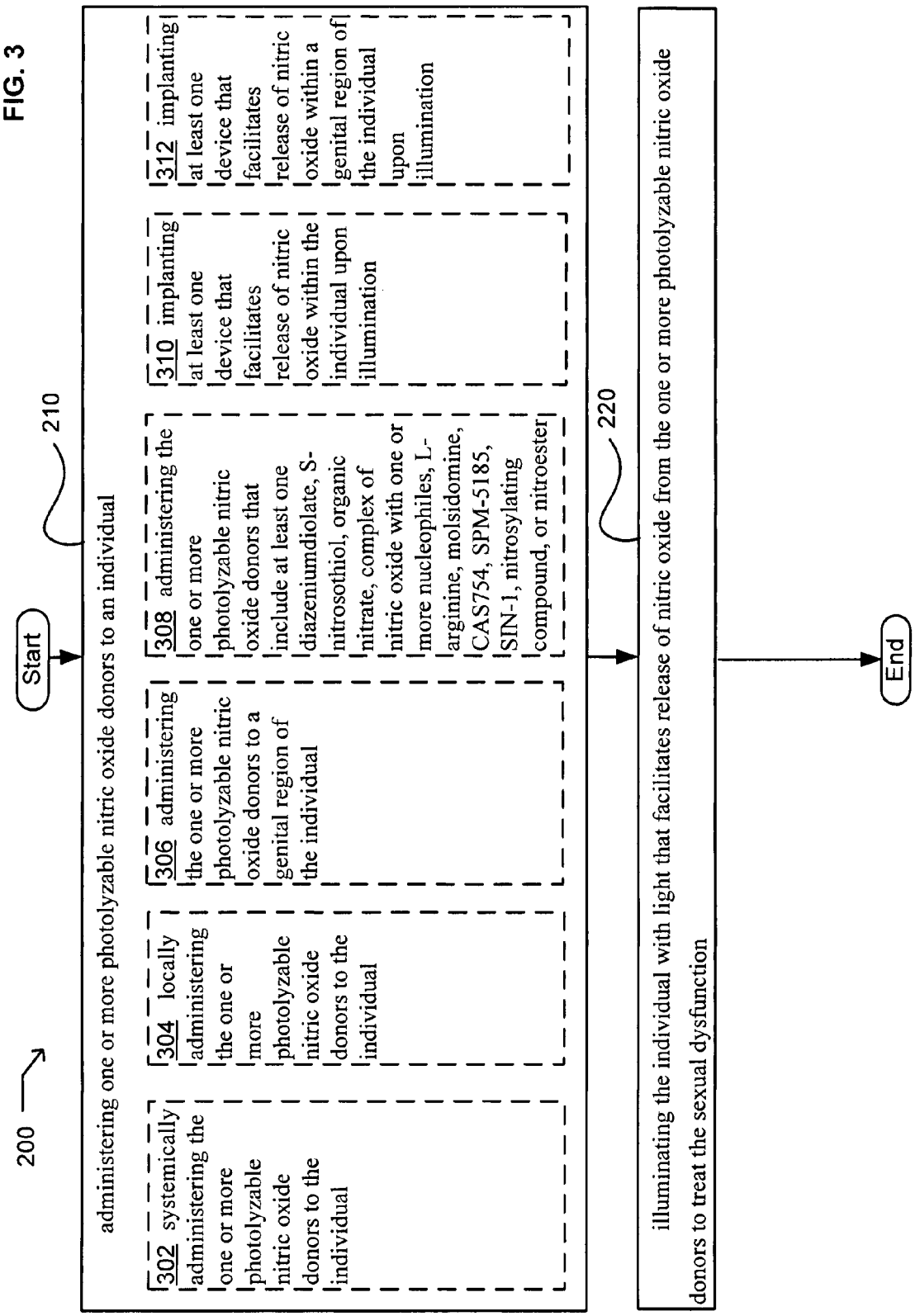
FIG. 3 illustrates alternate embodiments of the example operational flow of FIG. 2.

FIG. 3 illustrates alternative embodiments of the example operational flow 200 of FIG. 2. FIG. 3 illustrates example embodiments where the administering operation 210 may include at least one additional operation. Additional operations may include an operation 302, operation 304, operation 306, operation 308, operation 310, and/or operation 312.

At operation 302, the administering operation 210 may include systemically administering the one or more photolyzable nitric oxide donors to the individual. In some embodiments, one or more administration forms 110 may be used to systemically administer the one or more photolyzable nitric oxide donors 104 to the individual 108. For example, in some embodiments, one or more photolyzable nitric oxide donors 104 may be systemically delivered to an individual 108 through use of an administration form 110 that is formulated for oral administration to the individual 108. In some embodiments, one or more photolyzable nitric oxide donors 104 may be systemically delivered to an individual 108 through use of an administration form 110 that is formulated for pulmonary administration to the individual 108 (e.g., Wang et al., Can. J. Anesth., 50:839-846 (2003) and Gaston, Proc. Am. Thorac. Soc., 3:170-172 (2006)). In some embodiments, one or more photolyzable nitric oxide donors 104 may be formulated for topical delivery to an individual 108 (e.g., U.S. Pat. No. 6,287,601: herein incorporated by reference). In some embodiments, one or more photolyzable nitric oxide donors 104 may be systemically administered to an individual 108 through use of an implant that provides for release of the photolyzable nitric oxide donor 104 within the individual 108. Accordingly, numerous methods may be used to systemically administer one or more photolyzable nitric oxide donors 104 to an individual 108.

At operation 304, the administering operation 210 may include locally administering the one or more photolyzable nitric oxide donors to the individual. In some embodiments, one or more administration forms 110 may be used to locally administer the one or more photolyzable nitric oxide donors 104 to the individual 108. In some embodiments, one or more photolyzable nitric oxide donors 104 may be formulated for localized topical administration. For example, in some embodiments, one or more photolyzable nitric oxide donors 104 may be formulated as creams, lotions, gels, lubricants, and the like. In some embodiments, such formulations may include one or more photolyzable nitric oxide donors 104 in combination with one or more lipid based carriers. Such carriers have been described (e.g., U.S. Pat. No. 6,287,601; herein incorporated by reference). In some embodiments, such formulations may include one or more photolyzable nitric oxide donors 104 that are included within one or more vesicles, such as liposomes. Methods that may be used to create vesicles have been described (e.g., U.S. Pat. No. 5,814,666; herein incorporated by reference). In some embodiments, one or more photolyzable nitric oxide donors 104 may be locally administered within an individual 108 through use of one or more implants. Numerous types of implants may be used to locally administer photolyzable nitric oxide donors 104. In some embodiments, such implants may include one or more photolyzable nitric oxide donors 104 that are formulated with one or more biodegradable materials to form an implant (e.g., U.S. Pat. Nos. 5,736,152; 6,143,314; 6,773,714; herein incorporated by reference). In some embodiments, such implants may include one or more photolyzable nitric oxide donors 104 that are coupled to a polymeric material to form an implant. In some embodiments, such implants may include one or more photolyzable nitric oxide donors 104 that are included within an implantable matrix to form an implant. In some embodiments, one or more photolyzable nitric oxide donors 104 may be formulated for localized injection into an individual 108. In some embodiments, one or more photolyzable nitric oxide donors 104 may be locally administered to an individual 108 through use of electrophoresis. Accordingly, photolyzable nitric oxide donors 104 may be locally administered through use of numerous methodologies.

At operation 306, the administering operation 210 may include administering the one or more photolyzable nitric oxide donors to a genital region of the individual. In some embodiments, one or more administration forms 110 may be used to administer the one or more photolyzable nitric oxide donors 104 to a genital region of the individual 108. For example, in some embodiments, one or more photolyzable nitric oxide donors 104 may be formulated as creams, lotions, gels, lubricants, and the like. In some embodiments, such formulations may include one or more photolyzable nitric oxide donors 104 in combination with one or more lipid based carriers. Such carriers have been described (e.g., U.S. Pat. No. 6,287,601; herein incorporated by reference). In some embodiments, such formulations may include one or more photolyzable nitric oxide donors 104 that are included within one or more vesicles, such as liposomes. Methods that may be used to create vesicles have been described (e.g., U.S. Pat. No. 5,814,666; herein incorporated by reference). In some embodiments, one or more photolyzable nitric oxide donors 104 may be administered to a genital region of an individual 108 through use of one or more implants. Numerous types of implants may be used to administer one or more photolyzable nitric oxide donors 104 to the genitalia. In some embodiments, such implants may include one or more photolyzable nitric oxide donors 104 that are formulated with one or more biodegradable materials to form an implant (e.g., U.S. Pat. Nos. 5,736,152; 6,143,314; 6,773,714; herein incorporated by reference). In some embodiments, such implants may include one or more photolyzable nitric oxide donors 104 that are coupled to a polymeric material to form an implant. In some embodiments, such implants may include one or more photolyzable nitric oxide donors 104 that are included within an implantable matrix to form an implant. In some embodiments, one or more photolyzable nitric oxide donors 104 may be formulated for localized injection into a genital region of an individual 108. In some embodiments, one or more photolyzable nitric oxide donors 104 may be locally administered to the genitalia of an individual 108 through use of electrophoresis. Accordingly, photolyzable nitric oxide donors 104 may be administered through use of numerous methodologies.

At operation 308, the administering operation 210 may include administering the one or more photolyzable nitric oxide donors that include at least one diazeniumdiolate, S-nitrosothiol, organic nitrate, complex of nitric oxide with one or more nucleophiles, L-arginine, molsidomine, CAS754, SPM-5185, SIN-1, nitrosylating compound, or nitroester. In some embodiments, one or more administration forms 110 may be used to administer the one or more photolyzable nitric oxide donors 104 that include at least one diazeniumdiolate, S-nitrosothiol, organic nitrate, complex of nitric oxide 106 with one or more nucleophiles, L-arginine, molsidomine, CAS754, SPM-5185, SIN-1, nitrosylating compound, nitroester, or substantially any combination thereof.

At operation 310, the administering operation 210 may include implanting at least one device that facilitates release of nitric oxide within the individual upon illumination. In some embodiments, an implant associated entity may implant at least one device that facilitates release of nitric oxide 106 within the individual 108 upon illumination. In some embodiments, an implant associated entity may be a person associated with providing health care. Examples of such persons include, but are not limited to, physicians, nurses, clinical care persons, physician's assistants, hospitals, medical device representatives, and the like.

At operation 312, the administering operation 210 may include implanting at least one device that facilitates release of nitric oxide within a genital region of the individual upon illumination. In some embodiments, an implant associated entity may implant at least one device that facilitates release of nitric oxide 106 within a genital region of the individual 108 upon illumination. In some embodiments, an implant associated entity may be a person associated with providing health care. Examples of such persons include, but are not limited to, physicians, nurses, clinical care persons, physician's assistants, hospitals, medical device representatives, and the like.

Figure 4:
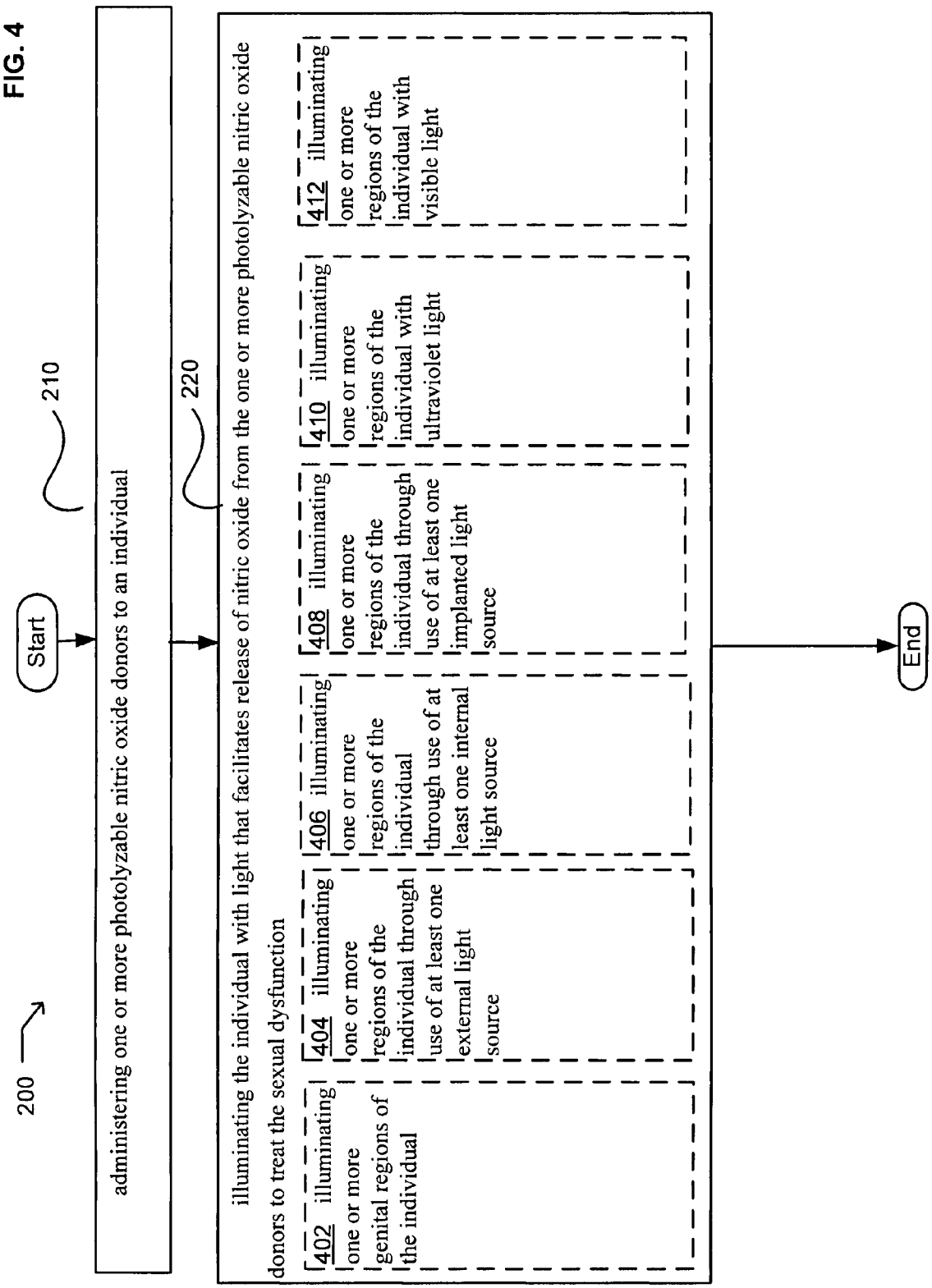
FIG. 4 illustrates alternate embodiments of the example operational flow of FIG. 2.

FIG. 4 illustrates alternative embodiments of the example operational flow 200 of FIG. 2. FIG. 4 illustrates example embodiments where the illuminating operation 220 may include at least one additional operation. Additional operations may include an operation 402, operation 404, operation 406, operation 408, operation 410, and/or operation 412.

At operation 402, the illuminating operation 220 may include illuminating one or more genital regions of the individual. In some embodiments, one or more light sources 102 may be used to illuminate one or more genital regions of the individual 108. In some embodiments, one or more light sources 102 may be used externally to illuminate one or more genital regions of an individual 108. In some embodiments, one or more internal light sources 102 may be used to illuminate one or more genital regions of an individual 108. One or more genital regions of an individual 108 may be illuminated with one or more light sources 102 that are configured in numerous ways. Examples of such configurations include, but are not limited to, condoms, wands, light sticks, flashlight configurations, lamps, gloves, underwear, implants, and the like. In some embodiments, one or more light sources 102 that emit a broad spectrum of light may be used to illuminate one or more genital regions of an individual 108. In some embodiments, one or more light sources 102 that emit a narrow spectrum of light may be used to illuminate one or more genital regions of an individual 108. In some embodiments, one or more light sources 102 that emit one or more wavelengths of light that are specifically selected to release nitric oxide 106 from one or more photolyzable nitric oxide donors 104 may be emitted. In some embodiments, one or more light sources 102 may emit light that does not include one or more wavelengths of light. In some embodiments, one or more light sources 102 may emit light that is selected to avoid and/or reduce damage to structures and/or tissues of an individual 108. For example, in some embodiments, one or more light sources 102 may emit light that does not include wavelengths of light that are absorbed by nucleic acids. In some embodiments, one or more light sources 102 may emit light that does not include wavelengths of light that are absorbed by polypeptides. In some embodiments, one or more light sources 102 may emit light that does not include one or more wavelengths of light within the following range: 250-320 nm. For example, in some embodiments, one or more light sources 102 may not emit 260 nm light. In some embodiments, one or more light sources 102 may not emit 280 nm light. In some embodiments, one or more light sources 102 may not emit 260 nm light or 280 nm light. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse.

At operation 404, the illuminating operation 220 may include illuminating one or more regions of the individual through use of at least one external light source. In some embodiments, one or more light sources 102 may be used to illuminate one or more regions of the individual 108 through use of at least one external light source 102. One or more regions of an individual 108 may be illuminated with one or more light sources 102 that are configured in numerous ways. Examples of such configurations include, but are not limited to, condoms, wands, light sticks, flashlight configurations, lamps, gloves, underwear, and the like. In some embodiments, one or more light sources 102 that emit a broad spectrum of light may be used to illuminate one or more regions of an individual 108. In some embodiments, one or more light sources 102 that emit a narrow spectrum of light may be used to illuminate one or more regions of an individual 108. In some embodiments, one or more light sources 102 that emit one or more wavelengths of light that are specifically selected to release nitric oxide 106 from one or more photolyzable nitric oxide donors 104 may be emitted. In some embodiments, one or more light sources 102 may emit light that does not include one or more wavelengths of light. In some embodiments, one or more light sources 102 may emit light that is selected to avoid and/or reduce damage to structures and/or tissues of an individual 108. For example, in some embodiments, one or more light sources 102 may emit light that does not include wavelengths of light that are absorbed by nucleic acids. In some embodiments, one or more light sources 102 may emit light that does not include wavelengths of light that are absorbed by polypeptides. In some embodiments, one or more light sources 102 may emit light that does not include one or more wavelengths of light within the following range: 250-320 nm. For example, in some embodiments, one or more light sources 102 may not emit 260 nm light. In some embodiments, one or more light sources 102 may not emit 280 nm light. In some embodiments, one or more light sources 102 may not emit 260 nm light or 280 nm light. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse.

At operation 406, the illuminating operation 220 may include illuminating one or more regions of the individual through use of at least one internal light source. In some embodiments, one or more light sources 102 may be used to illuminate one or more regions of the individual 108 through use of at least one internal light source 102. One or more regions of an individual 108 may be illuminated with one or more light sources 102 that are configured in numerous ways. Examples of such configurations include, but are not limited to, wands, light sticks, implants, and the like. In some embodiments, one or more light sources 102 that emit a broad spectrum of light may be used to illuminate one or more regions of an individual 108. In some embodiments, one or more light sources 102 that emit a narrow spectrum of light may be used to illuminate one or more regions of an individual 108. In some embodiments, one or more light sources 102 that emit one or more wavelengths of light that are specifically selected to release nitric oxide 106 from one or more photolyzable nitric oxide donors 104 may be emitted. In some embodiments, one or more light sources 102 may emit light that does not include one or more wavelengths of light. In some embodiments, one or more light sources 102 may emit light that is selected to avoid and/or reduce damage to structures and/or tissues of an individual 108. For example, in some embodiments, one or more light sources 102 may emit light that does not include wavelengths of light that are absorbed by nucleic acids. In some embodiments, one or more light sources 102 may emit light that does not include wavelengths of light that are absorbed by polypeptides. In some embodiments, one or more light sources 102 may emit light that does not include one or more wavelengths of light within the following range: 250-320 nm. For example, in some embodiments, one or more light sources 102 may not emit 260 nm light. In some embodiments, one or more light sources 102 may not emit 280 nm light. In some embodiments, one or more light sources 102 may not emit 260 nm light or 280 nm light. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse.

At operation 408, the illuminating operation 220 may include illuminating one or more regions of the individual through use of at least one implanted light source. In some embodiments, one or more light sources 102 may be used to illuminate one or more regions of the individual 108 through use of at least one implanted light source 102. Implanted light sources 102 may be configured in numerous ways. In some embodiments, one or more implanted light sources 102 may be configured as small beads (e.g., U.S. Pat. No. 5,571,152; herein incorporated by reference). In some embodiments, such light sources 102 may be implanted by injection. In some embodiments, one or more light sources 102 may include one or more fiber optic fibers that may be used to deliver light to one or more regions of an individual 108. For example, in some embodiments, such light emitting implants may be positioned within the corpus cavernosa of the penis. In some embodiments, one or more light sources 102 may emit fluorescent light. In some embodiments, one or more light sources 102 may emit phosphorescent light. In some embodiments, one or more implanted light sources 102 may emit light through chemiluminescence. In some embodiments, one or more implanted light sources 102 that emit a broad spectrum of light may be used to illuminate one or more regions of an individual 108. In some embodiments, one or more implanted light sources 102 that emit a narrow spectrum of light may be used to illuminate one or more regions of an individual 108. In some embodiments, one or more implanted light sources 102 that emit one or more wavelengths of light that are specifically selected to release nitric oxide 106 from one or more photolyzable nitric oxide donors 104 may be emitted. In some embodiments, one or more implanted light sources 102 may emit light that does not include one or more wavelengths of light. In some embodiments, one or more implanted light sources 102 may emit light that is selected to avoid and/or reduce damage to structures and/or tissues of an individual 108. For example, in some embodiments, one or more implanted light sources 102 may emit light that does not include wavelengths of light that are absorbed by nucleic acids. In some embodiments, one or more implanted light sources 102 may emit light that does not include wavelengths of light that are absorbed by polypeptides. In some embodiments, one or more implanted light sources 102 may emit light that does not include one or more wavelengths of light within the following range: 250-320 nm. For example, in some embodiments, one or more implanted light sources 102 may not emit 260 nm light. In some embodiments, one or more implanted light sources 102 may not emit 280 nm light. In some embodiments, one or more implanted light sources 102 may not emit 260 nm light or 280 nm light. Accordingly, numerous combinations of wavelengths of light may be excluded from emission by one or more implanted light sources 102. In some embodiments, light may be emitted continuously. In some embodiments, light may be emitted as a flash. In some embodiments, light may be emitted alternately as continuous light and a flash. In some embodiments, light may be emitted as a pulse.

At operation 410, the illuminating operation 220 may include illuminating one or more regions of the individual with ultraviolet light. In some embodiments, one or more light sources 102 may be used to illuminate one or more regions of the individual 108 with ultraviolet light. In some embodiments, one or more light sources 102 may emit a broad spectrum of ultraviolet light. In some embodiments, one or more light sources 102 may emit a narrow spectrum of ultraviolet light. In some embodiments, one or more light sources 102 that emit one or more wavelengths of ultraviolet light that are specifically selected to release nitric oxide 106 from one or more photolyzable nitric oxide donors 104. In some embodiments, one or more light sources 102 may emit ultraviolet light that does not include one or more wavelengths of light. In some embodiments, one or more light sources 102 may emit ultraviolet light that is selected to avoid and/or reduce damage to structures and/or tissues of an individual 108. For example, in some embodiments, one or more light sources 102 may emit ultraviolet light that does not include wavelengths of light that are absorbed by nucleic acids. In some embodiments, one or more light sources 102 may emit ultraviolet light that does not include wavelengths of light that are absorbed by polypeptides. In some embodiments, one or more light sources 102 may emit light that does not include one or more wavelengths of ultraviolet light within the following range: 250-320 nm. For example, in some embodiments, one or more light sources 102 may not emit 260 nm light. In some embodiments, one or more light sources 102 may not emit 280 nm light. In some embodiments, one or more light sources 102 may not emit 260 nm light or 280 nm light. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof.

At operation 412, the illuminating operation 220 may include illuminating one or more regions of the individual with visible light. In some embodiments, one or more light sources 102 may be used to illuminate one or more regions of the individual 108 with visible light. In some embodiments, one or more light sources 102 may emit a broad spectrum of visible light. In some embodiments, one or more light sources 102 may emit a narrow spectrum of visible light. In some embodiments, one or more light sources 102 may emit one or more wavelengths of visible light that are specifically selected to release nitric oxide 106 from one or more photolyzable nitric oxide donors 104. In some embodiments, one or more light sources 102 may emit visible light that does not include one or more wavelengths of light. In some embodiments, one or more light sources 102 may emit visible light that is selected to avoid and/or reduce damage to structures and/or tissues of an individual 108. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the visible light may be upconverted.

Figure 5:
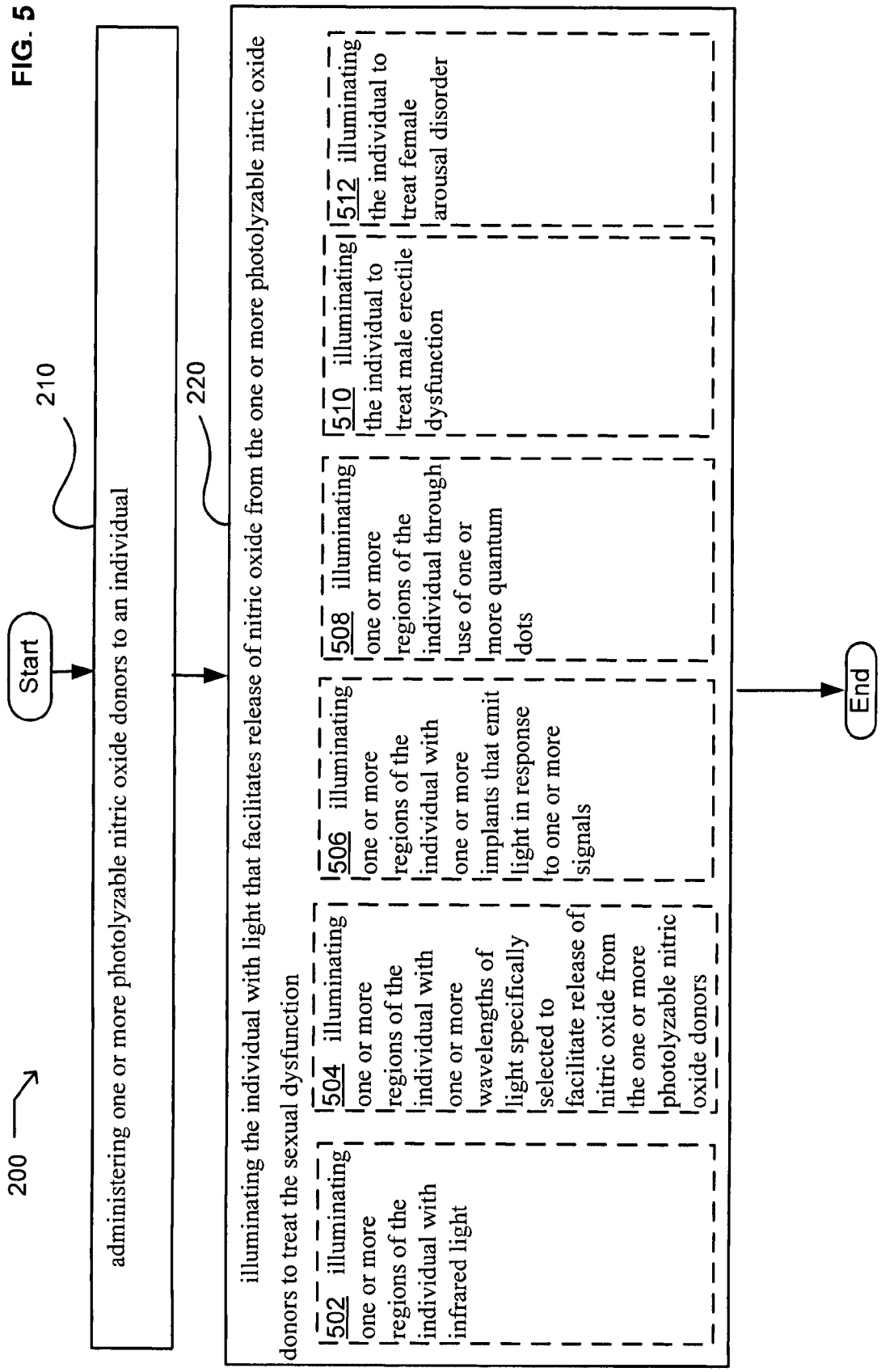
FIG. 5 illustrates alternate embodiments of the example operational flow of FIG. 2.

FIG. 5 illustrates alternative embodiments of the example operational flow 200 of FIG. 2. FIG. 5 illustrates example embodiments where the illuminating operation 220 may include at least one additional operation. Additional operations may include an operation 502, operation 504, operation 506, operation 508, operation 510, and/or operation 512.

At operation 502, the illuminating operation 220 may include illuminating one or more regions of the individual with infrared light. In some embodiments, one or more light sources 102 may be used to illuminate one or more regions of the individual 108 with infrared light. In some embodiments, one or more light sources 102 may emit a broad spectrum of infrared light. In some embodiments, one or more light sources 102 may emit a narrow spectrum of infrared light. In some embodiments, one or more light sources 102 may emit one or more wavelengths of infrared light that are specifically selected to release nitric oxide 106 from one or more photolyzable nitric oxide donors 104. In some embodiments, one or more light sources 102 may emit infrared light that does not include one or more wavelengths of light. In some embodiments, one or more light sources 102 may emit infrared light that is selected to avoid and/or reduce damage to structures and/or tissues of an individual 108. Accordingly, numerous combinations of wavelengths of light may be excluded from emission by one or more light sources 102. In some embodiments, light may be emitted continuously. In some embodiments, light may be emitted as a flash. In some embodiments, light may be emitted alternately as continuous light and a flash. In some embodiments, light may be emitted as a pulse. In some embodiments, light may be emitted continuously, as a flash, as a pulse, or substantially any combination thereof. In some embodiments, the infrared light may be upconverted.

At operation 504, the illuminating operation 220 may include illuminating one or more regions of the individual with one or more wavelengths of light specifically selected to facilitate release of nitric oxide from the one or more photolyzable nitric oxide donors. In some embodiments, one or more light sources 102 may be used to illuminate one or more regions of the individual 108 with one or more wavelengths of light specifically selected to facilitate release of nitric oxide 106 from the one or more photolyzable nitric oxide donors 104. For example, in some embodiments, one or more light sources 102 may be configured to emit light that includes one or more wavelengths of light that correspond to the absorption maximum for one or more nitric oxide donors. Examples of nitric oxide donors and their associated $\lambda_{max}$ (nm) are provided in Table I below. Accordingly, one or more light sources 102 may be configured to emit numerous wavelengths of light.

TABLE I

Example Nitric Oxide Donors

| Compound Name | $\lambda_{max}$ (nm) |
|---|---|
| $O^2$-(Acetoxymethyl) 1-(N,N-Diethylamino)diazen-1-ium-1,2-diolate | 230 |
| $O^2$-(Acetoxymethyl) 1-(Pyrrolidin-1-yl)diazen-1-ium-1,2-diolate | 256 |
| Sodium 1-(N-Benzyl-N-methylamino)diazen-1-ium-1,2-diolate | 252 |
| $O^2$-[(2,3,4,6-Tetra-O-acetyl)-β-D-glucosyl] 1-[4-(2,3-Dihydroxypropyl)piperazin-1 | 232 |
| Sodium 1-[4-(2,3-Dihydroxypropyl)piperazin-1-yl-]diazen-1-ium-1,2-diolate | 248.5 |
| $O^2$-Methyl 1-[(4-Carboxamido)piperidin-1-yl]diazen-1-ium-1,2-diolate | 241 |
| $O^2$-(2-Chloropyrimidin-4-yl) 1-(Pyrrolidin-1-yl)diazen-1-ium-1,2-diolate | 274 |
| $O^2$-(2,4-Dinitrophenyl) 1-[4-(N,N-Diethylcarboxamido)piperazin-1-yl]diazen-1-ium-1,2-diolate | 300 |
| $O^2$-(2,4-Dinitrophenyl) 1-(4-Nicotinylpiperazin-1-yl)diazen-1-ium-1,2-diolate | 300 |
| $O^2$-(2,4-Dinitrophenyl) 1-{4-[2-(4-{2-Methylpropyl}phenyl)propionyl]piperazin-1-yl}diazen-1-ium-1,2-diolate | 300 |
| Sodium 1-(4-Benzyloxycarbonylpiperazin-1-yl)diazen-1-ium-1,2-diolate | 252 |
| $O^2$-(2,4-Dinitrophenyl) 1-[4-(tert-Butoxycarbonyl)piperazin-1-yl]diazen-1-ium-1,2-diolate | 299 |
| $O^2$-(2,4-Dinitrophenyl) 1-(4-Acetylpiperazin-1-yl)diazen-1-ium-1,2-diolate | 394 |
| $O^2$-(2,4-Dinitrophenyl) 1-[4-(Succinimidoxycarbonyl)piperazin-1-yl]diazen-1-ium-1,2-diolate | 300 |
| $O^2$-(2,4-Dinitrophenyl) 1-(Piperazin-1-yl)diazen-1-ium-1,2-diolate, Hydrochloride Salt | 297 |
| $O^2$-(2,3,4,6-Tetra-O-acetyl-D-glucopyranosyl) 1-(N,N-Diethylamino)diazen-1-ium-1,2-diolate | 228 |
| $O^2$-(-D-Glucopyranosyl) 1-(N,N-Diethylamino)diazen-1-ium-1,2-diolate | 228 |
| Sodium (Z)-1-(N,N-Diethylamino)diazen-1-ium-1,2-diolate | 250 |
| 1-[N-(2-Aminoethyl)-N-(2-ammonioethyl)amino]diazen-1-ium-1,2-diolate | 252 |
| Sodium 1-(N,N-Dimethylamino)diazen-1-ium-1,2-diolate | 250 |

TABLE I-continued

Example Nitric Oxide Donors

| Compound Name | $\lambda_{max}$ (nm) |
|---|---|
| $O^2$-(2,4-Dinitrophenyl) 1-(N,N-Diethylamino)diazen-1-ium-1,2-diolate | 302 |
| 1-[N-(3-Aminopropyl)-N-(3-ammoniopropyl]diazen-1-ium-1,2-diolate | 252 |
| 1-[N-(3-Aminopropyl)-N-(3-ammoniopropyl]diazen-1-ium-1,2-diolate | 252 |
| Bis-diazeniumdiolated benzyl imidate dehydrate | 264 |
| p-Bisdiazeniumdiolated benzene | 316 |
| Methane Trisdiazeniumdiolate trihydrate | 316 |
| $O^2$-(β-D-Glucopyranosyl) 1-(Isopropylamino)diazen-1-ium-1,2-diolate | 278 |
| Sodium 1-[4-(5-Dimethylamino-1-naphthalenesulfonyl)piperazin-1-yl]diazen-1-ium-1,2-diolate | 344 |
| 1-(2-Methyl-1-propenyl)piperidine diazeniumdiolate | 246 |
| 1-(2-Methyl-1-propenyl)pyrrolidine diazeniumdiolate | 246 |
| $O^2$-Vinyl 1-(Pyrrolidin-1-yl)diazen-1-ium-1,2-diolate | 268 |
| 1-{N-[3-Aminopropyl]-N-[4-(3-aminopropylammoniobutyl)]}diazen-1-ium-1,2-diolate | 252 |
| Disodium 1-[(2-Carboxylato)pyrrolidin-1-yl]diazen-1-ium-1,2-diolate | 252 |
| 1-[N-(3-Ammoniopropyl)-N-(n-propyl)amino]diazen-1-ium-1,2-diolate | 250 |
| (Z)-1-{N-Methyl-N-[6-(N-methylammoniohexyl)amino]}diazen-1-ium-1,2-diolate | 250 |
| $O^2$-(2,4-Dinitrophenyl) 1-[(4-Ethoxycarbonyl)piperazin-1-yl]diazen-1-ium-1,2-diolate | 300 |

At operation 506, the illuminating operation 220 may include illuminating one or more regions of the individual with one or more light sources that emit light in response to one or more signals. In some embodiments, one or more implants illuminate one or more regions of the individual 108 with one or more light sources that emit light in response to one or more signals 114. In some embodiments, one or more light sources may be external. In some embodiments, one or more light sources may be internal. In some embodiments, one or more light sources may be an implant. In some embodiments, one or more implants may emit light upon receiving one or more signals 114 that are transmitted by one or more receivers. In some embodiments, the one or more signals 114 may include numerous types of information. Examples of such information include, but are not limited to, information related to light intensity, light duration, one or more wavelengths of light to be emitted, and the like. In some embodiments, one or more implants may receive one or more signals 114 from one or more transmitters that are physically coupled to the one or more implants. In some embodiments, one or more implants may receive one or more signals 114 from one or more transmitters that are remotely coupled to the one or more implants.

At operation 508, the illuminating operation 220 may include illuminating one or more regions of the individual through use of one or more quantum dots. In some embodiments, one or more light sources 102 may be used to illuminate one or more regions of the individual 108 through use of one or more quantum dots. In some embodiments, one or more light sources 102 may be associated with one or more quantum dots. In some embodiments, quantum dots may be tuned to absorb light that is emitted by one or more light sources 102 and emit light that facilitates release of nitric oxide 106 from one or more photolyzable nitric oxide donors 104. In some embodiments, quantum dots may be tuned to emit light that specifically facilitates release of nitric oxide 106 from one or more photolyzable nitric oxide donors 104. For example, in some embodiments, one or more quantum dots may emit light that includes wavelengths of light that correspond to the absorption maximum of one or more photolyzable nitric oxide donors 104.

At operation 510, the illuminating operation 220 may include illuminating the individual to treat male erectile dysfunction. In some embodiments, one or more light sources 102 may be used to illuminate the individual 108 to treat male erectile dysfunction. In some embodiments, one or more light sources 102 may be used to externally illuminate one or more regions of a male. In some embodiments, one or more light sources 102 may be used to externally illuminate one or more genital regions of a male. In some embodiments, one or more light sources 102 may be used to internally illuminate one or more genital regions of a male. For example, in some embodiments, one or more light sources 102 may be inserted into the urethra of a male. In some embodiments, one or more implanted light sources 102 may be used to illuminate a male.

At operation 512, the illuminating operation 220 may include illuminating the individual to treat female arousal disorder. In some embodiments, one or more light sources 102 may be used to illuminate the individual 108 to treat female arousal disorder. In some embodiments, one or more light sources 102 may be used to externally illuminate one or more regions of a female. In some embodiments, one or more light sources 102 may be used to externally illuminate one or more genital regions of a female. In some embodiments, one or more light sources 102 may be used to internally illuminate one or more genital regions of a female. For example, in some embodiments, one or more light sources 102 may be inserted into the urethra of a female. In some embodiments, one or more implanted light sources 102 may be used to illuminate a female.

Figure 6:
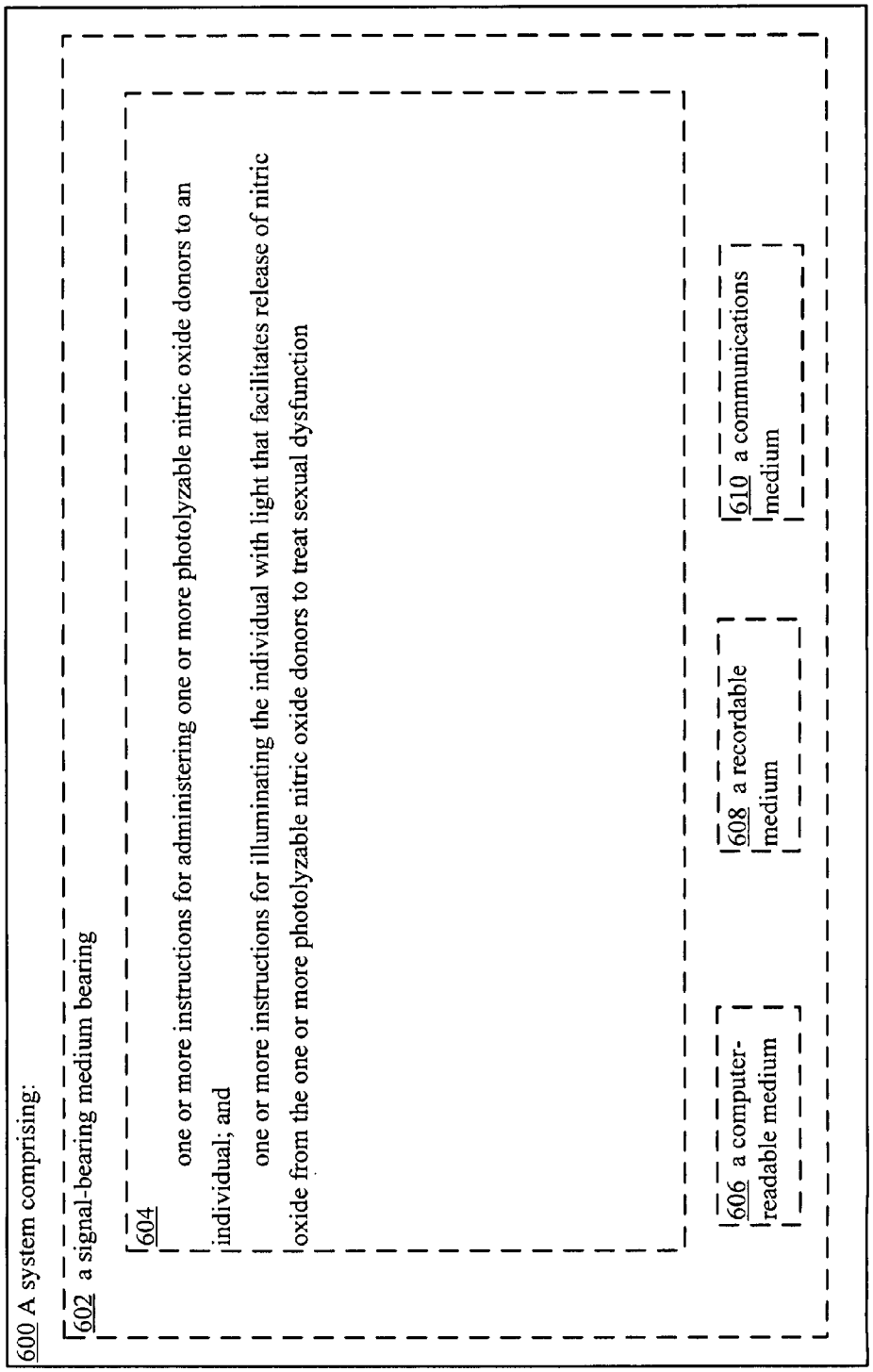
FIG. 6 illustrates an example system 600 in which embodiments may be implemented.

FIG. 6 illustrates a partial view of a system 600 that includes a computer program 604 for executing a computer process on a computing device. An embodiment of system 600 is provided using a signal-bearing medium 602 bearing one or more instructions for administering one or more photolyzable nitric oxide donors 104 to an individual 108 and one or more instructions for illuminating the individual 108 with light that facilitates release of nitric oxide 106 from the one or more photolyzable nitric oxide donors 104 to treat sexual dysfunction. The one or more instructions may be, for example, computer executable and/or logic-implemented instructions. In some embodiments, the signal-bearing medium 602 may include a computer-readable medium 606. In some embodiments, the signal-bearing medium 602 may include a recordable medium 608. In some embodiments, the signal-bearing medium 602 may include a communications medium 610. Instructions for administering one or more photolyzable nitric oxide donors 104 to an individual 108 may include numerous types of information. Examples of such information include, but are not limited to, the type of administration form 110 to use to administer one or more photolyzable nitric oxide donors 104 to an individual 108, dosage of one or more photolyzable nitric oxide donors 104, time of administration for one or more photolyzable nitric oxide donors 104, contraindications associated with the one or more photolyzable nitric oxide donors 104, side-effects of the one or more photolyzable nitric oxide donors 104, warnings associated with use of the one or more photolyzable nitric oxide donors 104, conditions (e.g., mental, physical, etc.) that may be treated with one or more photolyzable nitric oxide donors 104, and the like. Instructions for illuminating an individual 108 with light that facilitates release of nitric oxide 106 from one or more photolyzable nitric oxide donors 104 to treat sexual dysfunction may include numerous types of information. Examples of such information include, but are not limited to, information associated with one or more light sources 102 that may be used to illuminate an individual 108, information associated with one or more light sources 102 that may be used in association with one or more photolyzable nitric oxide donors 104, length of time that an individual 108 should be illuminated, intensity of light that should be used to illuminate an individual 108, benefits that may result from using one or more light sources 102 in association with one or more photolyzable nitric oxide donors 104, and the like. In some embodiments, the instructions may include advertising materials.

Figure 7:
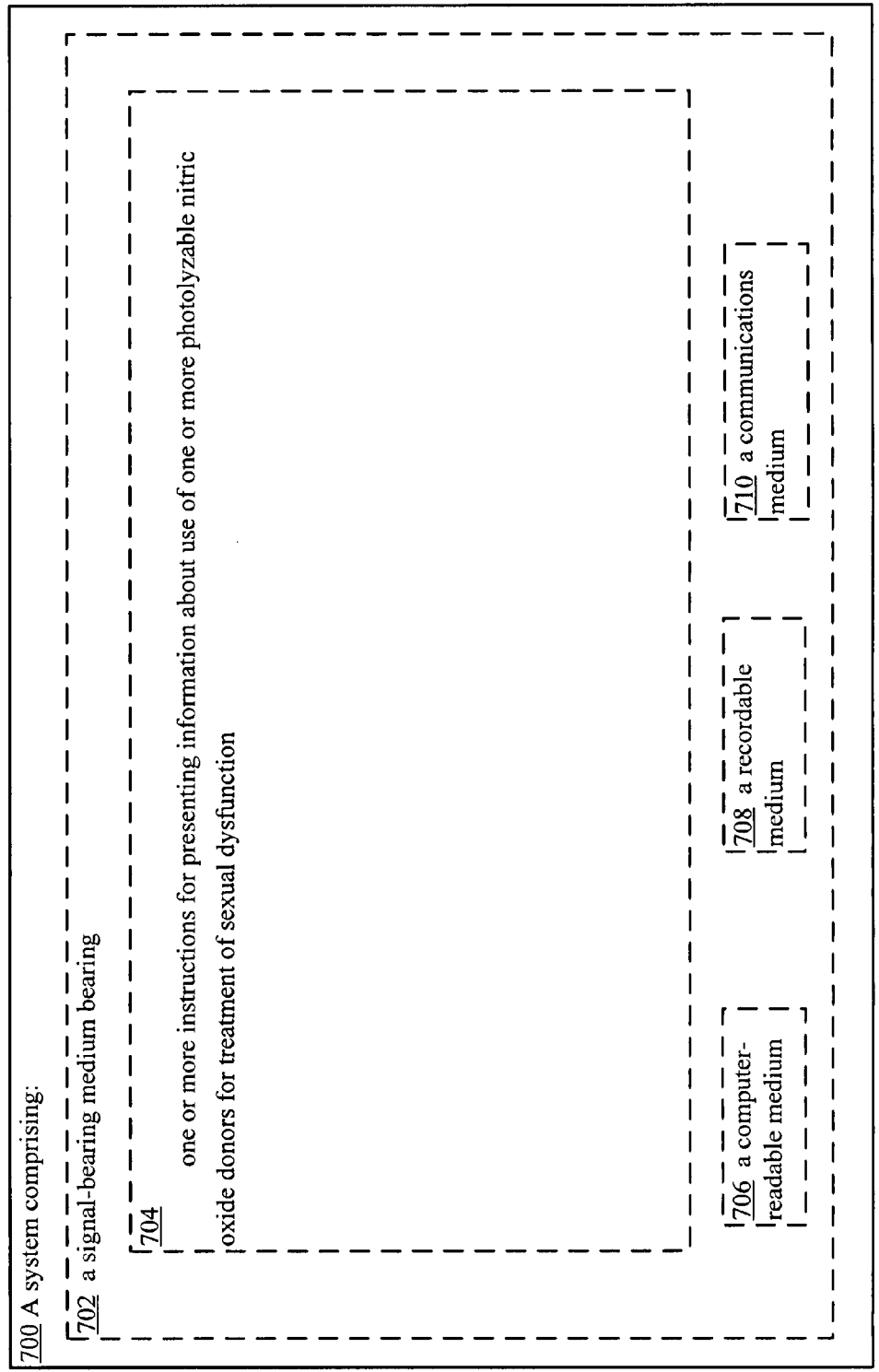
FIG. 7 illustrates an example system 700 in which embodiments may be implemented.

FIG. 7 illustrates a partial view of a system 700 that includes a computer program 704 for executing a computer process on a computing device. An embodiment of the system 700 is provided using a signal-bearing medium 702 bearing one or more instructions for presenting information about use of one or more photolyzable nitric oxide donors 104 for treatment of sexual dysfunction. The one or more instructions may be, for example, computer executable and/or logic-implemented instructions. In some embodiments, the signal-bearing medium 702 may include a computer-readable medium 706. In some embodiments, the signal-bearing medium 702 may include a recordable medium 708. In some embodiments, the signal-bearing medium 702 may include a communications medium 710. Instructions for presenting information about use of one or more photolyzable nitric oxide donors 104 for treatment of sexual dysfunction may include numerous types of information. Examples of such information include, but are not limited to, the type of administration form 110 to use to administer the one or more photolyzable nitric oxide donors 104, dosage of the one or more photolyzable nitric oxide donors 104, time of administration for the one or more photolyzable nitric oxide donors 104, contraindications associated with the one or more photolyzable nitric oxide donors 104, side-effects of the one or more photolyzable nitric oxide donors 104, warnings associated with use of the one or more photolyzable nitric oxide donors 104, conditions (e.g., mental, physical, etc.) that may be treated with one or more photolyzable nitric oxide donors 104, and the like. In some embodiments, the instructions may include advertising materials.

Figure 8:
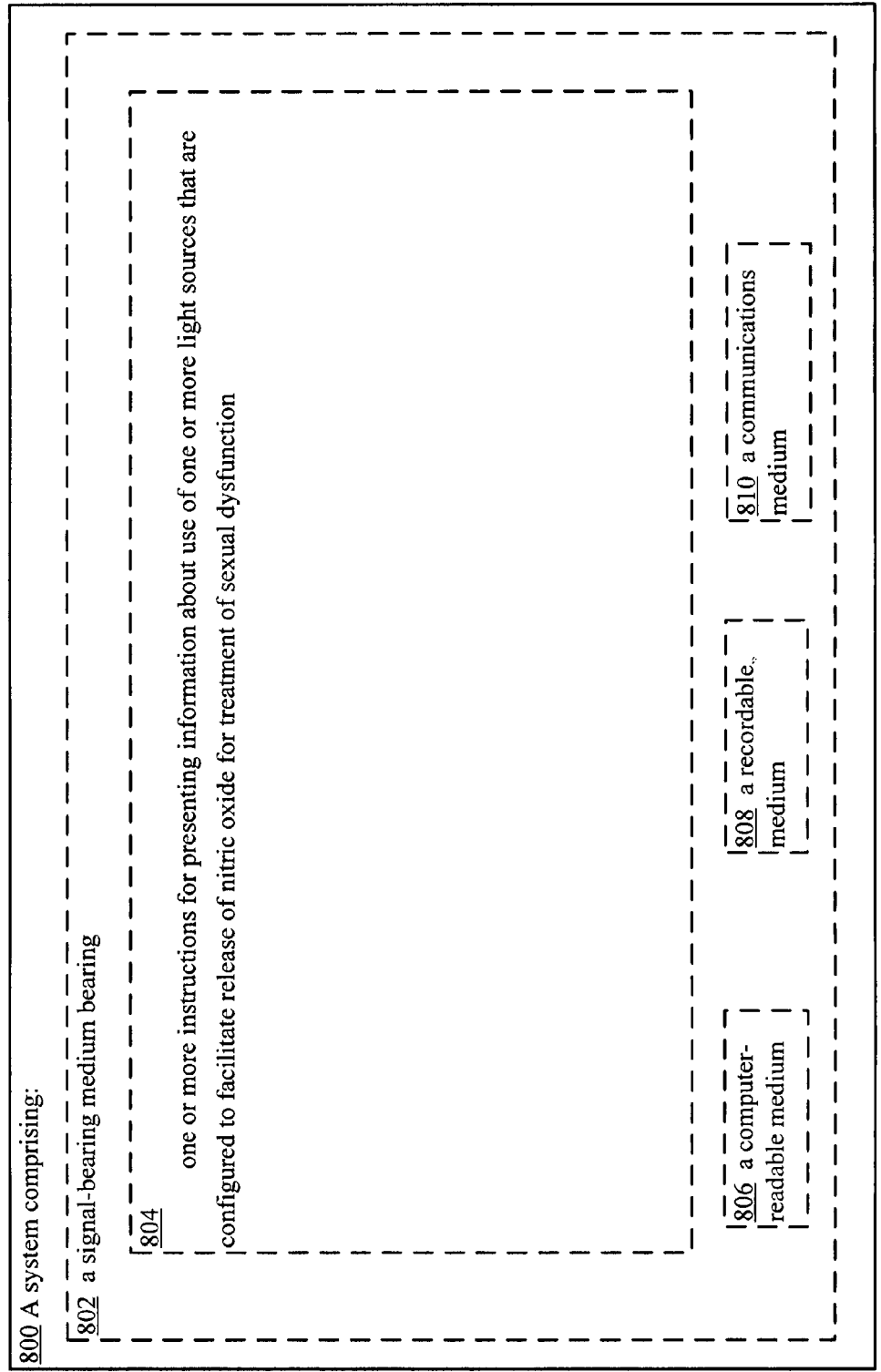
FIG. 8 illustrates an example system 800 in which embodiments may be implemented.

FIG. 8 illustrates a partial view of a system 800 that includes a computer program 804 for executing a computer process on a computing device. An embodiment of the system 800 is provided using a signal-bearing medium 802 bearing one or more instructions for presenting information about use of one or more light sources 102 that are configured to facilitate release of nitric oxide 106 for treatment of sexual dysfunction. The one or more instructions may be, for example, computer executable and/or logic-implemented instructions. In some embodiments, the signal-bearing medium 802 may include a computer-readable medium 806. In some embodiments, the signal-bearing medium 802 may include a recordable medium 808. In some embodiments, the signal-bearing medium 802 may include a communications medium 810. Instructions for presenting information about use of one or more light sources 102 for treatment of sexual dysfunction may include numerous types of information. Examples of such information include, but are not limited to, information associated with one or more light sources 102 that may be used to treat sexual dysfunction, information associated with one or more light sources 102 that may be used in association with one or more photolyzable nitric oxide donors 104 to treat sexual dysfunction, length of time that an individual 108 should be illuminated to treat sexual dysfunction, intensity of light that should be used to illuminate an individual 108 to treat sexual dysfunction, and the like. In some embodiments, the instructions may include advertising materials.

With respect to the use of substantially any plural and/or singular terms herein, those having skill in the art can translate from the plural to the singular and/or from the singular to the plural as is appropriate to the context and/or application. The various singular/plural permutations are not expressly set forth herein for sake of clarity.

While particular aspects of the present subject matter described herein have been shown and described, it will be apparent to those skilled in the art that, based upon the teachings herein, changes and modifications may be made without departing from the subject matter described herein and its broader aspects and, therefore, the appended claims are to encompass within their scope all such changes and modifications as are within the true spirit and scope of the subject matter described herein. Furthermore, it is to be understood that the invention is defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Those having skill in the art will recognize that the state of the art has progressed to the point where there is little distinction left between hardware and software implementations of aspects of systems; the use of hardware or software is generally (but not always, in that in certain contexts the choice between hardware and software can become significant) a design choice representing cost vs. efficiency tradeoffs. Those having skill in the art will appreciate that there are various vehicles by which processes and/or systems and/or other technologies described herein can be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; alternatively, if flexibility is paramount, the implementer may opt for a mainly software implementation; or, yet again alternatively, the implementer may opt for some combination of hardware, software, and/or firmware. Hence, there are several possible vehicles by which the processes and/or devices and/or other technologies described herein may be effected, none of which is inherently superior to the other in that any vehicle to be utilized is a choice dependent upon the context in which the vehicle will be deployed and the specific concerns (e.g., speed, flexibility, or predictability) of the implementer, any of which may vary. Those skilled in the art will recognize that optical aspects of implementations will typically employ optically-oriented hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples can be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal-bearing medium used to actually carry out the distribution. Examples of a signal-bearing medium include, but are not limited to, the following: a recordable type medium such as a floppy disk, a hard disk drive, a Compact Disc (CD), a Digital Video Disk (DVD), a digital tape, a computer memory, etc.; and a transmission type medium such as a digital and/or an analog communication medium (e.g., a fiber optic cable, a waveguide, a wired communications link, a wireless communication link, etc.).

In a general sense, those skilled in the art will recognize that the various embodiments described herein can be implemented, individually and/or collectively, by various types of electromechanical systems having a wide range of electrical components such as hardware, software, firmware, or virtually any combination thereof, and a wide range of components that may impart mechanical force or motion such as rigid bodies, spring or torsional bodies, hydraulics, and electro-magnetically actuated devices, or virtually any combination thereof. Consequently, as used herein "electro-mechanical system" includes, but is not limited to, electrical circuitry operably coupled with a transducer (e.g., an actuator, a motor, a piezoelectric crystal, etc.), electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), electrical circuitry forming a communications device (e.g., a modem, communications switch, or optical-electrical equipment), and any non-electrical analog thereto, such as optical or other analogs. Those skilled in the art will also appreciate that examples of electromechanical systems include but are not limited to a variety of consumer electronics systems, as well as other systems such as motorized transport systems, factory automation systems, security systems, and communication/computing systems. Those skilled in the art will recognize that electromechanical as used herein is not necessarily limited to a system that has both electrical and mechanical actuation except as context may dictate otherwise.

In a general sense, those skilled in the art will recognize that the various aspects described herein which can be implemented, individually and/or collectively, by a wide range of hardware, software, firmware, or any combination thereof can be viewed as being composed of various types of "electrical circuitry." Consequently, as used herein "electrical circuitry" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

Those skilled in the art will recognize that it is common within the art to implement devices and/or processes and/or systems in the fashion(s) set forth herein, and thereafter use engineering and/or business practices to integrate such implemented devices and/or processes and/or systems into more comprehensive devices and/or processes and/or systems. That is, at least a portion of the devices and/or processes and/or systems described herein can be integrated into other devices and/or processes and/or systems via a reasonable amount of experimentation. Those having skill in the art will recognize that examples of such other devices and/or processes and/or systems might include—as appropriate to context and application—all or part of devices and/or processes and/or systems of (a) an air conveyance (e.g., an airplane, rocket, hovercraft, helicopter, etc.), (b) a ground conveyance (e.g., a car, truck, locomotive, tank, armored personnel carrier, etc.), (c) a building (e.g., a home, warehouse, office, etc.), (d) an appliance (e.g., a refrigerator, a washing machine, a dryer, etc.), (e) a communications system (e.g., a networked system, a telephone system, a voice-over IP system, etc.), (f) a business entity (e.g., an Internet Service Provider (ISP) entity such as Comcast Cable, Quest, Southwestern Bell, etc), or (g) a wired/wireless services entity (e.g., such as Sprint, Cingular, Nextel, etc.), etc.

Although the user interface 118 is shown/described herein as a single illustrated figure that is associated with an individual 108, those skilled in the art will appreciate that a user interface 118 may be utilized by a user that is a representative of a human user, a robotic user (e.g., computational entity), and/or substantially any combination thereof (e.g., a user may be assisted by one or more robotic based systems). In addition, a user as set forth herein, although shown as a single entity may in fact be composed of two or more entities. Those skilled in the art will appreciate that, in general, the same may be said of "sender" and/or other entity-oriented terms as such terms are used herein.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components and/or wirelessly interactable and/or wirelessly interacting components and/or logically interacting and/or logically interactable components.

All publications, patents and patent applications cited herein are incorporated herein by reference. The foregoing specification has been described in relation to certain embodiments thereof, and many details have been set forth for purposes of illustration, however, it will be apparent to those skilled in the art that the invention is susceptible to additional embodiments and that certain of the details described herein may be varied considerably without departing from the basic principles of the invention.

What is claimed is:

1. A method for treating sexual dysfunction comprising:
    administering at least one of a lubricant, a gel, a cream, a lotion, or a jelly, that includes a photolyzable nitric oxide donor, to a genital region of an individual; and
    illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor.

2. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
    illuminating the genital region of the individual, using an internal light source that is configured to emit light that includes a wavelength of light that corresponds to an absorption maximum for the photolyzable nitric oxide donor, to facilitate release of nitric oxide from the photolyzable nitric oxide donor.

3. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
    illuminating the genital region of the individual, using an implanted light source that is configured to emit light that includes a wavelength of light that corresponds to an absorption maximum for the photolyzable nitric oxide donor, to facilitate release of nitric oxide from the photolyzable nitric oxide donor.

4. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
    illuminating the genital region of the individual, using an ultraviolet light source that is configured to emit light that includes a wavelength of light that corresponds to an absorption maximum for the photolyzable nitric oxide donor, to facilitate release of nitric oxide from the photolyzable nitric oxide donor.

5. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a visible light source that is configured to emit light that includes a wavelength of light that corresponds to an absorption maximum for the photolyzable nitric oxide donor, to facilitate release of nitric oxide from the photolyzable nitric oxide donor.

6. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using an infrared light source that is configured to emit light that includes a wavelength of light that corresponds to an absorption maximum for the photolyzable nitric oxide donor, to facilitate release of nitric oxide from the photolyzable nitric oxide donor.

7. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor, in response to one or more signals.

8. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor to treat male erectile dysfunction.

9. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor to treat female arousal disorder.

10. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using an implanted light source that is configured to emit light that includes a wavelength of light that corresponds to an absorption maximum for the photolyzable nitric oxide donor, to facilitate release of nitric oxide from the photolyzable nitric oxide donor, in response to one or more signals.

11. The method of claim 1, wherein the administering at least one of a lubricant, a gel, a cream, a lotion, or a jelly, that includes a photolyzable nitric oxide donor, to a genital region of an individual comprises:
administering at least one of a lubricant, a gel, a cream, a lotion, or a jelly, that includes at least one of the following types of photolyzable nitric oxide donors, to a genital region of an individual: diazeniumdiolate, S-nitrosothiol, organic nitrate, complex of nitric oxide with one or more nucleophiles, L-arginine, molsidomine, CAS754, SPM-5185, SIN-1, nitrosylating compound, or nitroester.

12. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using an external light source that is configured to emit light that includes a wavelength of light that corresponds to an absorption maximum for the photolyzable nitric oxide donor, to facilitate release of nitric oxide from the photolyzable nitric oxide donor.

13. The method of claim 1, wherein the administering at least one of a lubricant, a gel, a cream, a lotion, or a jelly, that includes a photolyzable nitric oxide donor, to a genital region of an individual comprises:
administering at least one of a lubricant, a gel, a cream, a lotion, or a jelly, that includes a first photolyzable nitric oxide donor and a second photolyzable nitric oxide donor, to a genital region of an individual.

14. The method of claim 13, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using a first light source that is configured to emit light that includes a wavelength of light that corresponds to an absorption maximum for the first photolyzable nitric oxide donor, to facilitate release of nitric oxide from the first photolyzable nitric oxide donor.

15. The method of claim 14, further comprising:
illuminating the genital region of the individual, using light that includes at least a wavelength of light that corresponds to an absorption maximum for the second photolyzable nitric oxide donor, to facilitate release of nitric oxide from the second photolyzable nitric oxide donor.

16. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:
illuminating the genital region of the individual, using a light source that is configured for vaginal insertion and that is configured to emit light that includes a wavelength of light that corresponds to an absorption maximum for the photolyzable nitric oxide donor, to facilitate release of nitric oxide from the photolyzable nitric oxide donor.

17. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a light source that is configured as at least one of a lamp, a flashlight, a wand, a ring, underwear, or a condom and that is configured to emit light that includes a wavelength of light that corresponds to an absorption maximum for the photolyzable nitric oxide donor, to facilitate release of nitric oxide from the photolyzable nitric oxide donor.

18. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

internally illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor.

19. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

externally illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor.

20. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor, in response to activation of a switch associated with the light source.

21. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a light emitting diode (LED) that is configured to emit light that includes a wavelength of light that corresponds to an absorption maximum for the photolyzable nitric oxide donor, to facilitate release of nitric oxide from the photolyzable nitric oxide donor.

22. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a light source that is configured to emit, using an optical fiber, light that includes a wavelength of light that corresponds to an absorption maximum for the photolyzable nitric oxide donor, to facilitate release of nitric oxide from the photolyzable nitric oxide donor.

23. The method of claim 1, wherein the illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor comprises:

illuminating the genital region of the individual, using a light source that is configured to emit light that includes a wavelength of light that corresponds to an absorption maximum for the photolyzable nitric oxide donor, to facilitate release of nitric oxide from the photolyzable nitric oxide donor to facilitate achievement of an erection, increase rigidity of an erection, increase blood flow, increase lubrication, increase clitoral vasocongestion, and/or increase duration of an erection.

24. The method of claim 1, wherein the sexual dysfunction results from at least one of surgery, physical injury, pharmaceutical use, or age.

25. The method of claim 1, wherein the sexual dysfunction is due to a mental condition.

26. The method of claim 1, wherein the method is performed at least partly by the individual.

\* \* \* \* \*